(12) United States Patent
Fine et al.

(10) Patent No.: US 10,720,755 B2
(45) Date of Patent: Jul. 21, 2020

(54) ENSEMBLE-AVERAGED MEASUREMENT OF STOCHASTIC MOTION BY CURRENT-MODULATING OF VCSEL WAVELENGTH

(71) Applicants: Ilya Fine, Rehovot (IL); Alexander Kaminsky, Tbilisi (GE)

(72) Inventors: Ilya Fine, Rehovot (IL); Alexander Kaminsky, Tbilisi (GE)

(73) Assignee: ELFI-TECH LTD., Rehovot (IL)

( * ) Notice: Subject to any disclaimer, the term of this patent is extended or adjusted under 35 U.S.C. 154(b) by 0 days.

(21) Appl. No.: 15/890,388

(22) Filed: Feb. 7, 2018

(65) Prior Publication Data

US 2019/0312411 A1  Oct. 10, 2019

(51) Int. Cl.
*H01S 5/183* (2006.01)
*G01N 15/14* (2006.01)
*G01N 33/86* (2006.01)

(52) U.S. Cl.
CPC ......... *H01S 5/183* (2013.01); *G01N 15/1434* (2013.01); *G01N 33/86* (2013.01); *G01N 2015/1445* (2013.01)

(58) Field of Classification Search
CPC .... H01S 5/183; G01N 33/86; G01N 15/1434; G01N 2015/1445
See application file for complete search history.

(56) References Cited

U.S. PATENT DOCUMENTS

| 5,495,850 | A  | * | 3/1996  | Zuckerman   | A61B 5/14555 356/41 |
|-----------|----|---|---------|-------------|---------------------|
| 5,522,389 | A  | * | 6/1996  | Fischer     | A61B 5/14539 356/41 |
| 6,784,981 | B1 | * | 8/2004  | Roche       | G01N 1/38 356/336   |
| 7,356,364 | B1 | * | 4/2008  | Bullock     | A61B 5/14532 600/310|
| 7,688,427 | B2 | * | 3/2010  | Cox         | G01N 15/1456 356/39 |
| 7,911,617 | B2 | * | 3/2011  | Padmanabhan | G01N 15/1484 356/246|
| 9,091,625 | B2 | * | 7/2015  | Wu          | G01N 21/6428        |
| 9,103,759 | B2 | * | 8/2015  | Wu          | G01N 15/147         |
| 2007/0009386 | A1 | * | 1/2007 | Padmanabhan | B01L 3/502776 422/68.1 |
| 2007/0116347 | A1 | * | 5/2007 | Hong        | G06T 7/143 382/131  |
| 2008/0247429 | A1 | * | 10/2008| Colbourne   | H01S 5/0622 372/26  |
| 2009/0054767 | A1 | * | 2/2009 | Telischak   | A61B 5/0071 600/431 |

(Continued)

*Primary Examiner* — Mohamed K Amara
(74) *Attorney, Agent, or Firm* — Marc Van Dyke; Momentum IP Group

(57) ABSTRACT

Embodiments of the invention relate to a method and apparatus for measuring at least one parameter that is (i) descriptive of stochastic motion of suspended particles within a fluid; and/or (ii) is a rheological property of the fluid or of the suspension; (iii) describes a concentration of suspended particles within the fluid; and/or (iv) is a diffusion coefficient of the suspended particles and/or (iv) is a viscosity of the fluid or of the suspension; and/or (v) is a food aging or spoilage parameter and/or (vii) is an in-vivo or in-vitro blood coagulation parameter.

5 Claims, 24 Drawing Sheets

(56) References Cited

U.S. PATENT DOCUMENTS

| | | | |
|---|---|---|---|
| 2009/0209834 A1* | 8/2009 | Fine | A61B 5/14551 600/316 |
| 2011/0228254 A1* | 9/2011 | Ueno | G01S 17/325 356/5.09 |
| 2011/0270113 A1* | 11/2011 | Heyne | A61B 5/0836 600/531 |
| 2012/0002189 A1* | 1/2012 | Bengoechea Apezteguia | G01F 1/661 356/28.5 |
| 2013/0123639 A1* | 5/2013 | Ando | A61B 5/0059 600/473 |
| 2014/0094666 A1* | 4/2014 | Fine | A61B 5/7246 600/316 |
| 2014/0128744 A1* | 5/2014 | Cuccia | A61B 5/0064 600/476 |
| 2014/0336479 A1* | 11/2014 | Ando | A61B 5/4041 600/310 |
| 2017/0090031 A1* | 3/2017 | Bondy | G01S 17/89 |
| 2017/0273581 A1* | 9/2017 | Koppel | A61B 5/7282 |
| 2017/0315046 A1* | 11/2017 | Du | G01N 21/6428 |
| 2017/0322198 A1* | 11/2017 | Zelmanovic | G01N 21/532 |
| 2018/0110450 A1* | 4/2018 | Lamego | A61B 5/0004 |
| 2019/0150763 A1* | 5/2019 | Gladshtein | F16L 33/30 |

\* cited by examiner

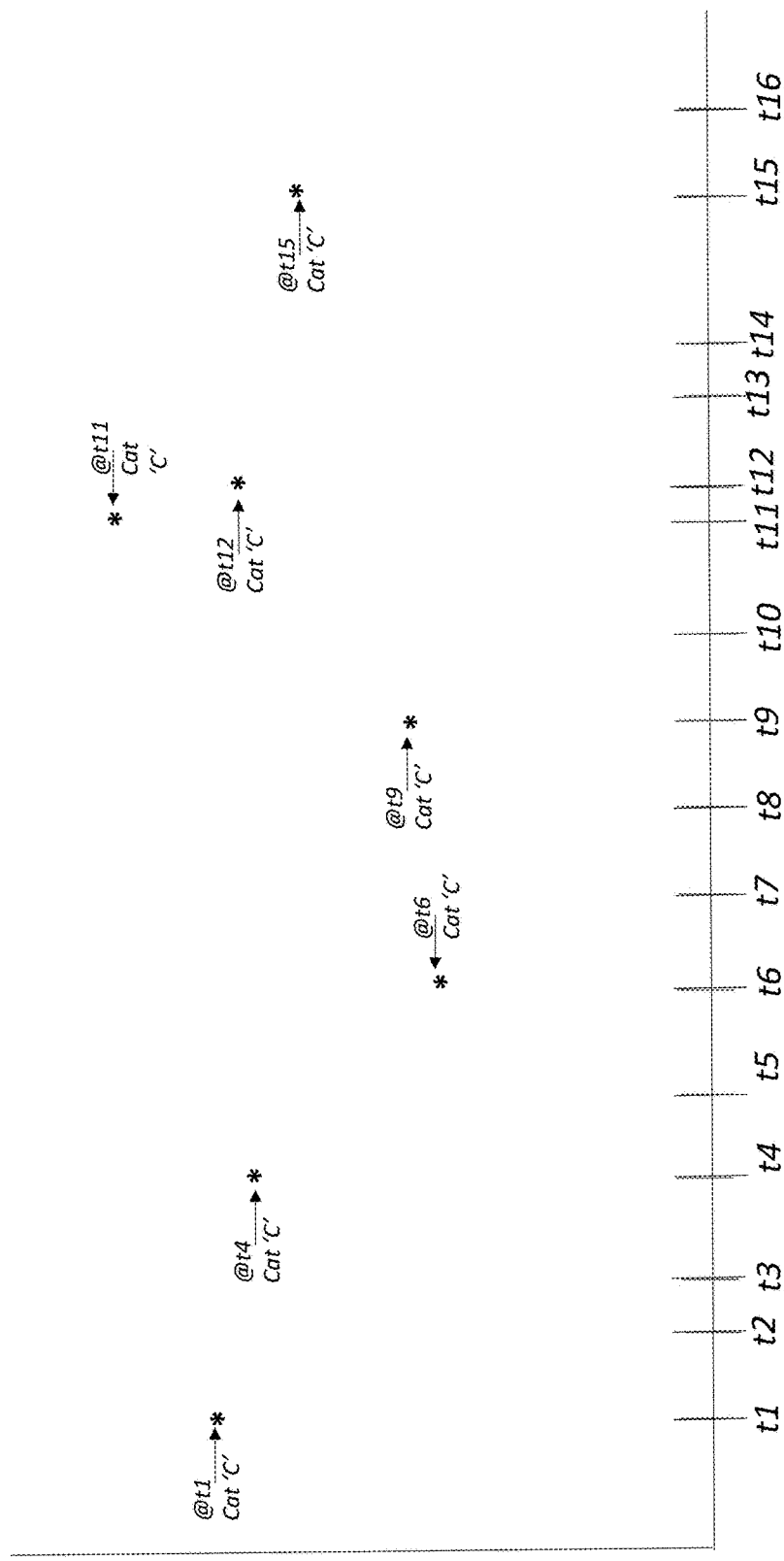

Element 148[4] of Fig. 1 according to one example "CATEGORY D"

EXAMPLE "Y"

ENSEMBLE-AVERAGED MEASUREMENT OF STOCHASTIC MOTION BY CURRENT-MODULATING OF VCSEL WAVELENGTH

Embodiments of the present invention relate to an apparatus and method for measuring a diffusion coefficient and/or rheological parameter and/or a parameter related to blood coagulation and/or fluid viscosity and/or a parameter related to blood coagulability by using the dynamic light scattering technique.

In some embodiments, a technique for the dynamic light scattering ensemble averaging is provided which (i) does not require mechanical movement of the measured sample relative to the optical system (or component(s) thereof) and/or (ii) does not require a relatively 'large' array of light detectors that are 'widely' distributed over various locations. In this way, the presently disclosed teachings are applicable for providing a 'micro-sensor' that is compact and practical—for example, for embedding in mobile phones, on a wrist-watch, or in a system including a cub which applies pressure (e.g. on a user's system).

Not wishing to be bound by theory, it is noted that certain stochastic physical and/or chemical processes are 'slow' and in order to accumulate a significant statistics over different system configuration a relatively 'long' period of time is required. One example is Brownian motion of red blood cells (RBCs) (i.e. which are relatively 'large' particles whose diffusion characteristic time is relatively 'slow') within quiescent, occluded blood. Because Brownian motion of suspended particles is a stochastic process, measurement of the diffusion coefficient (even a 'small' diffusion coefficient) may require acquisition of different data sets or ensembles that are statistically independent over each other. However, practical time limitations or fast dynamic of the measured system does not enable to accumulate sufficient statistically independent set of measurement points. Embodiments of the present invention provide a technique for acquiring different ensembles in a shorter period of time.

Once again, not wishing to be bound by theory, it is noted that this may be useful, for example, for measuring a parameter descriptive of (e.g. a rate of) blood coagulation where: (i) because blood coagulation is derived from and/or governed by diffusion of RBCs within occluded blood, the amount of time required to measure statistically independent ensembles may be relatively large and (ii) this relatively large amount of time may, in certain situations, exceed the characteristic time of blood coagulation, rendering DLS measurements of blood coagulation as difficult even over long periods of time.

BRIEF DESCRIPTION OF THE DRAWINGS

FIG. 11C illustrates the sample points of the sample set of FIG. 8 that are categorized into 'category C.'

BRIEF DESCRIPTION OF EMBODIMENTS

Figure 1A:
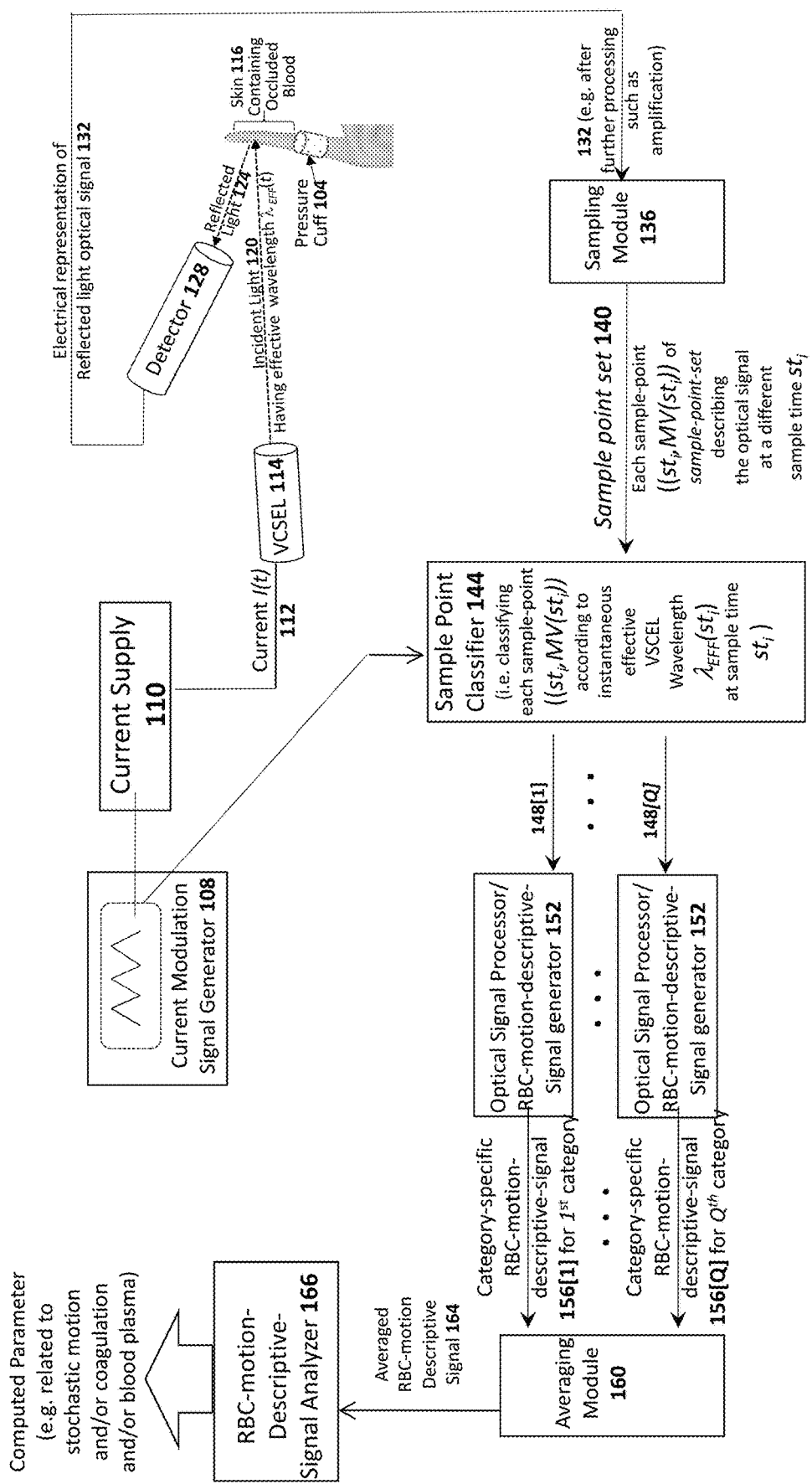
FIGS. 1A-1B are block diagrams of systems measuring parameters descriptive of or derived from stochastic motion.

FIG. 1A is a block diagram of a system for measuring parameters descriptive of or derived from stochastic motion (e.g. Brownian motion) of particles (e.g. red blood cells (RBCs)) suspended within a fluid (e.g. blood plasma). Time varying current I(t) is supplied to a VCSEL 114 so as to temporally vary an effective wavelength of light $\lambda_{EFF}$ of light emitted by VCSEL. For example, a current supply 110 supplies the current according to a current modulation signal generated by current modulation signal generator 108 (e.g. implemented as an executing software module). Light is reflected by a skin 116 of subject's finger (e.g. within the finger are blood vessels containing occluded blood—the blood is occlude by pressure cuff 104).

Reflected and/or scattered light 124 scattered by and/or dynamically modulated by the skin blood particles 116 is received by detector 128 which converts an optical signal of the received light into an electrical representation 132 thereof. This electrical representation is processed by sampling module 136 to generate a sample point set (referred to as Sample Point Set 140) describing the optical signal carried by the reflected light 124 at different sample times.

In particular, Sampled point set is a set of sample points $\{(st_1, MV(st_1)), (st_2, MV(st_2)), \ldots (st_P, MV(st_P))\}$ where: (i) each sample point is an ordered pair $(st_i, MV(st_i))$; (ii) MV is an abbreviation of 'measurement value' and is a measurement (at sample time $st_i$) of an electrical representation 132 of the optical signal carried by reflected light 124; (iii) st is an abbreviation for sample time where $st_1$ is a first sample time, $st_2$ is a second sample time, and so on—sample time $st_i$ is the ith sample time where i is a positive integer less than or equal top); and (iv) the cardinality Sampled_measurement_set of is P where P≥2, (e.g. P≥10 or P≥100 or P≥1000 or P≥1000).

As will be explained below with reference to FIG. 9, each sample point $(st_i, MV(st_i))$ relates to a measurement value MV of the electrical representation 132 of the optical signal carried by reflected light 124 at a respective sample time $st_i$—at this sample time $st_i$ the effective wavelength $\lambda_{EFF}$ of VCSEL 114 is $\lambda_{EFF}(st_i)$.

It is possible to classify each sample point $(st_i, MV(st_i))$ according to its sample time—in particular, according to the effective wavelength $\lambda_{EFF}$ of VCSEL 114 at the sample time $st_i$ of the sample point $(st_i, MV(st_i))$. Thus, when the wavelength $\lambda_{EFF}(st_i)$ is in a first range $[\lambda_1, \lambda_2](\lambda_2 > \lambda_1)$ then the sample point $(st_i, MV(st_i))$ is categorized into a first category, when the wavelength $\lambda_{EFF}(st_i)$ is in a second range $[\lambda_3, \lambda_4]$ $(\lambda_4 > \lambda_3 > \lambda_2)$ then the sample point $(st_i, MV(st_i))$ is categorized into a second category.

Sample point classifier 144 classifies each sample point $(st_i, MV(st_i))$ according to its sample time $st_i$—in particular, sample point classifier 144 classifies each sample point $(st_i, MV(st_i))$ into one of Q (Q is a positive integer≥2) categories based on (e.g. based only on) sample point sample-time $st_i$. These categories are referred to as VCSEL-wavelength categories $\{Cat_1 \ldots Cat_Q\}$—e.g. $Cat_1$ may be $[\lambda_1, \lambda_2]$, $Cat_2$ may be $[\lambda_3, \lambda_4]$ and so on.

In FIG. 1, 148[1] is the set of sample points $(st_i, MV(st_i))$ (e.g. a first subset of Sampled_point_set 140) where sample points of the set 148[1] are categorized into VCSEL-wavelength category $Cat_1$, 148[2] is the set of sample points $(st_i, MV(st_i))$ (e.g. a second subset of Sampled_point_set 140) where sample points of the set 148[2] are categorized into VCSEL-wavelength category $Cat_2$.

Thus, classifier 144 works as follows—each given VCSEL-wavelength category $Cat_j$ of the plurality of VCSEL-wavelength categories $\{Cat_1 \ldots Cat_Q\}$ forming, from the sample points classified into the given VCSEL-wavelength category Cat(j), a respective VCSEL-wavelength-category-specific sample point set 148[1], 148[2], ... VCSEL_wavelength_specific_sample_points (Cat(j)) of sample points $\{(st_{1\_CAT(j)}, MV(st_{1\_CAT(j)}), (st_{2\_CAT(j)}, MV(st_{2\_CAT(j)}), \ldots\}$ (i.e. this is the content of 148[j] for the jth category).

Figure 9:
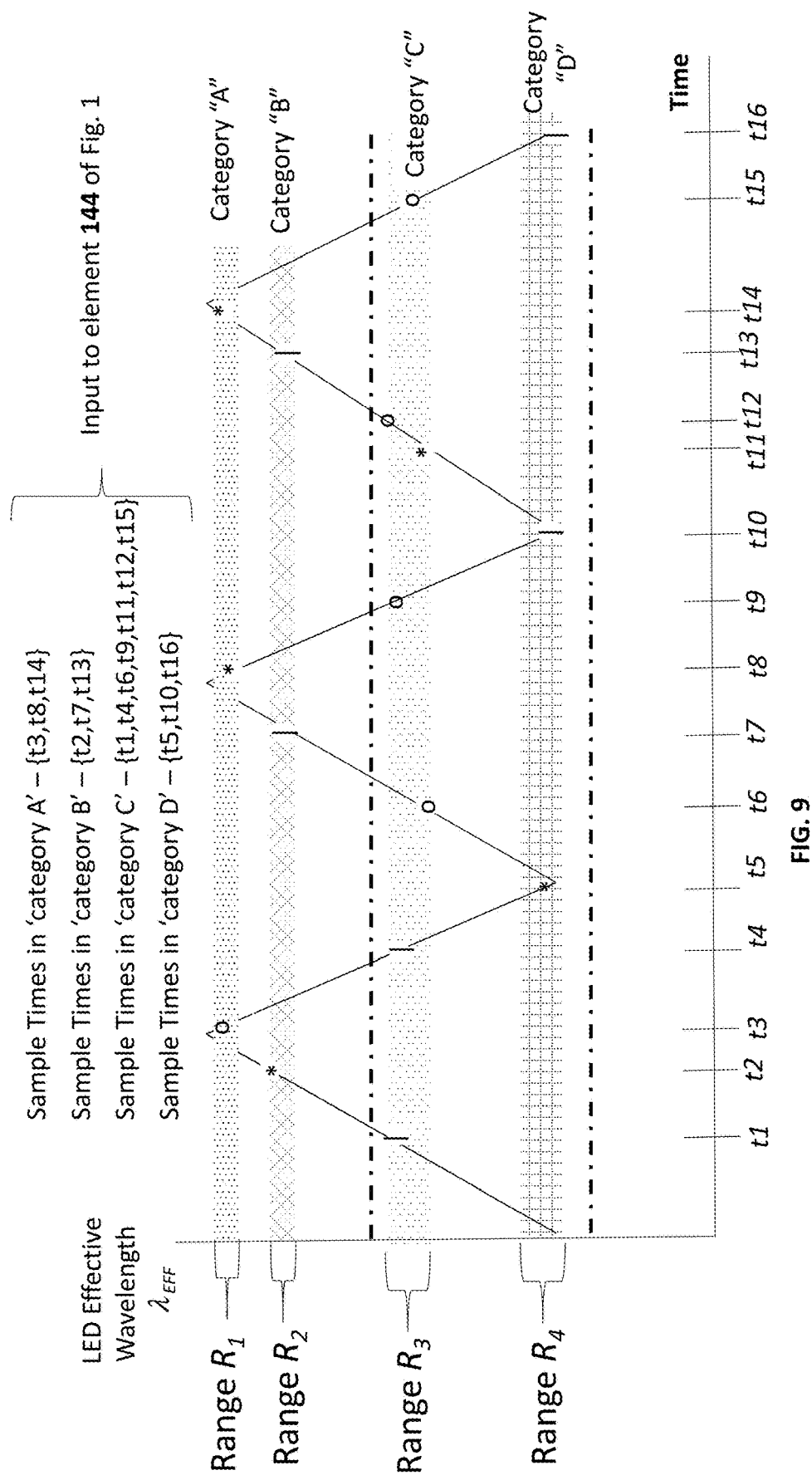
Figure 11A:
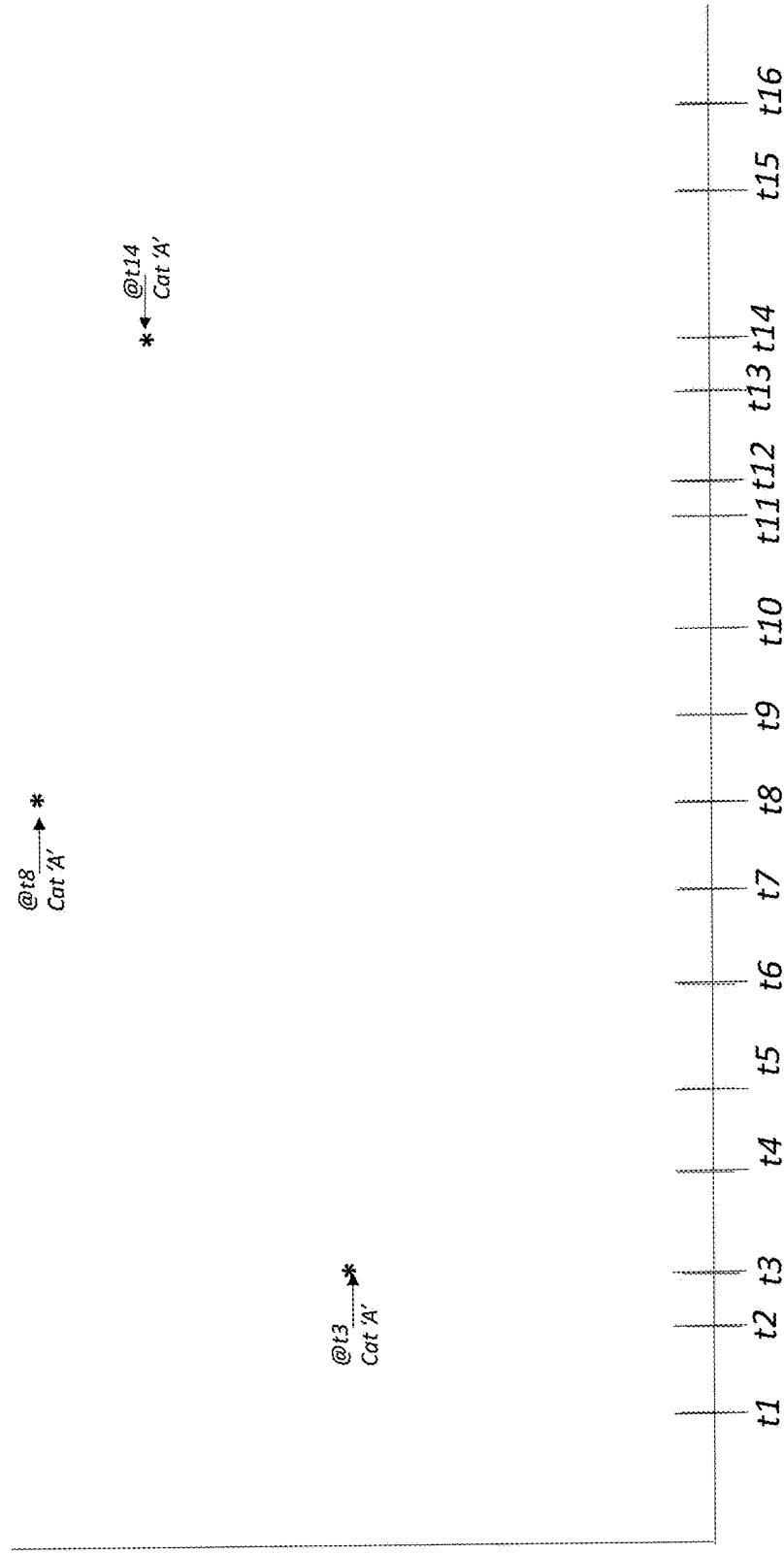
FIG. 11A illustrates the sample points of the sample set of FIG. 8 that are categorized into 'category A.'

In the example of FIGS. 9 and 11A (j=1), 1_Cat(1)=3, 2_Cat(1)=8, and 3_Cat(1)=14.

Figure 11B:
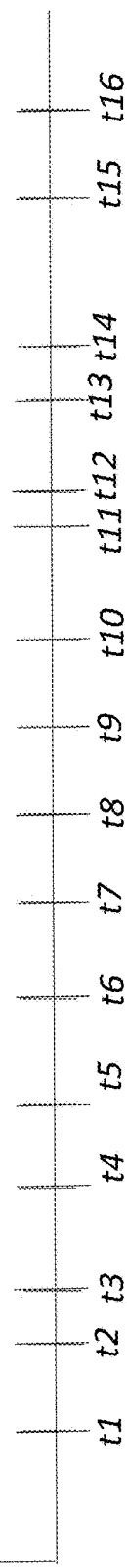
FIG. 11B illustrates the sample points of the sample set of FIG. 8 that are categorized into 'category B.'

In the example of FIGS. 9 and 11B (j=2), 1_Cat(2)=2, 2_Cat(2)=7, and 3_Cat(2)=13.

In the non-limiting example of FIG. 1, each of the sets 148[1], 148[2] ... 148[Q] is a subset of 148, and the sets 148[1], 148[2] ... 148[Q] are disjoint. Furthermore, in the non-limiting example of FIG. 1, each sample point $(st_i, MV(st_i))$ is categorized only according to its sample time $st_i$—i.e. only according to the value of $\lambda_{EFF}(st_i)$.

Each 148[i] of the sets 148[1], 148[2] ... 148[Q] is a different representation of the reflected light optical signal 132 propagated by the reflected light 124. In the example of FIG. 1, each set is processed separated by optical signal process/RBC-motion-descriptive signal generator 152. The input of optical signal process/RBC-motion-descriptive signal generator 152 is a representation of reflected light optical signal 132—the output of optical signal process/RBC-motion-descriptive signal generator 152 is a description of motion (e.g. stochastic motion such as Brownian or quasi-Brownian motion) of suspended particles (e.g. microparticles such as red blood cells (RBCs)) within a fluid (e.g. occluded blood plasma). In particular, the output of optical signal process/RBC-motion-descriptive signal generator 152 describes relative motion between suspended particles. In situations where the blood is pulsatile, the relative motion may describe shear of the pulsatile blood. In situations where the blood is occluded (e.g. FIG. 1), the relative motion may describe relative stochastic motion (e.g. Brownian motion) of the suspended particles (e.g. RBCs).

As taught in various prior art documents (each of which are incorporated by reference in their entirety) such as WO 2008/053474 and WO2012064326, optical signal process/RBC-motion-descriptive signal generator 152 may generate the RBC-motion-descriptive signal based upon autocorrelation and/or power-spectrum techniques. Any feature or combination of feature(s) disclosed herein may be combined with any feature or combination of feature(s) disclosed in WO 2008/053474 or WO2012064326.

In the example of FIG. 1A, each of 148[1], 148[2] ... 148[Q] is separately sent to optical signal process/RBC-motion-descriptive signal generator 152. The end result [see FIG. X] is Q RCB-motion-descriptive-signals, one per VCSEL-wavelength category $Cat_i$. These signals are sent to averaging module 160, which averages them (e.g. in some embodiments, a 'straight average'; in other embodiments a weighted average).

Figure 1B:
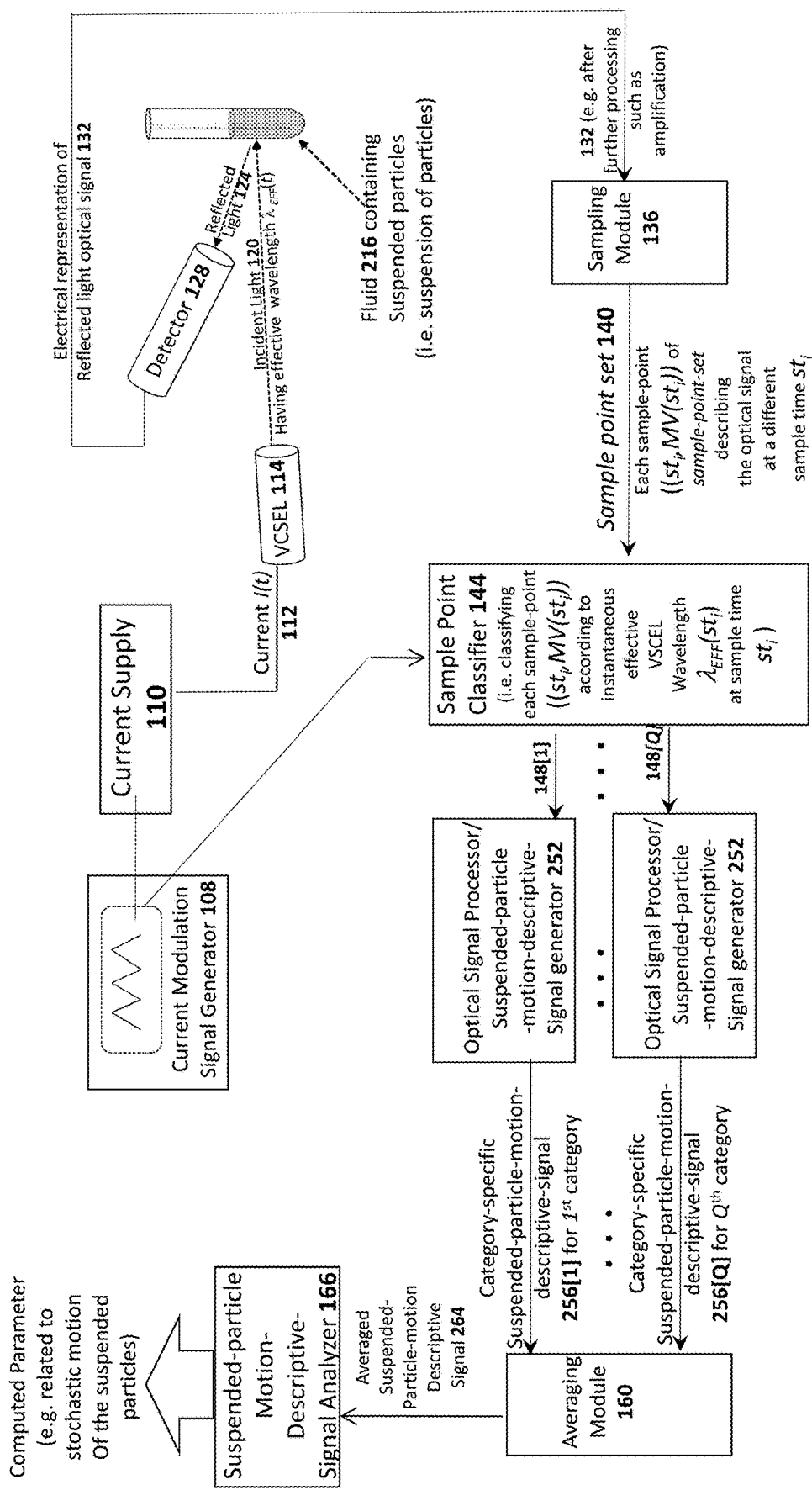

FIG. 1A relates to the specific case where the suspended particles are RBCs and the fluid is occluded blood plasma and the measurement is performed 'in vitro'—this is not a limitation. FIG. 1B relates another case where the suspension can be anything (e.g. in vivo or in vitro blood or a food product or any other suspension) and the particles can be any particle (e.g. RBC or any other particle that undergoes, for example, diffusion and/or stochastic motion and/or Brownian motion).

Throughout the present document, the specific example of RBCs suspended in blood plasma is discussed—however, the teachings may be applied to any suspension including but not limited to blood.

Figure 2A:
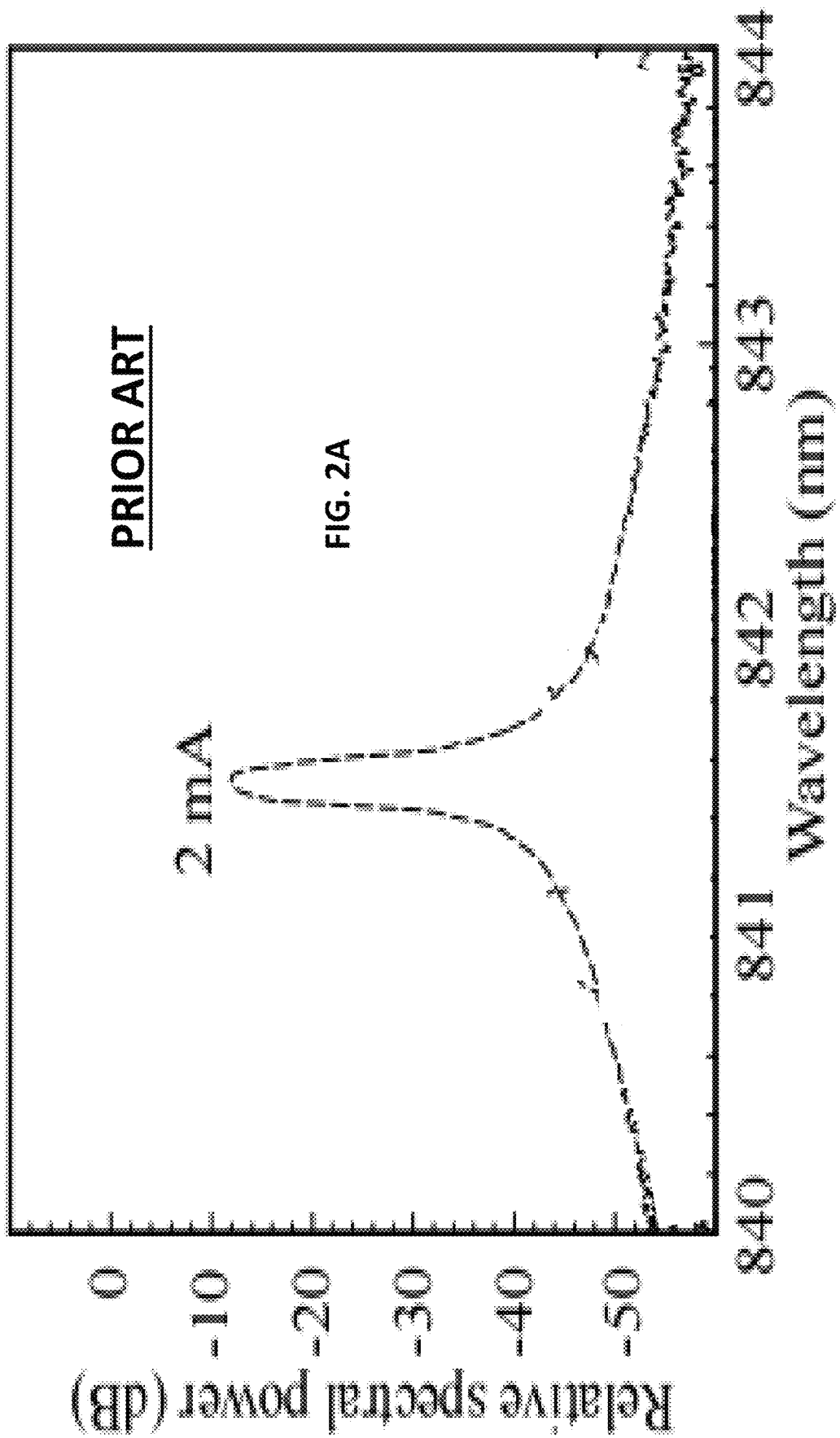
FIG. 2A (PRIOR ART) illustrates a relative spectral power (Db) of a VSCEL (vertical-cavity surface-emitting laser) as a function of wavelength for one particular VSCEL when supplied with 2 mA of electrical current.
Figure 2B:
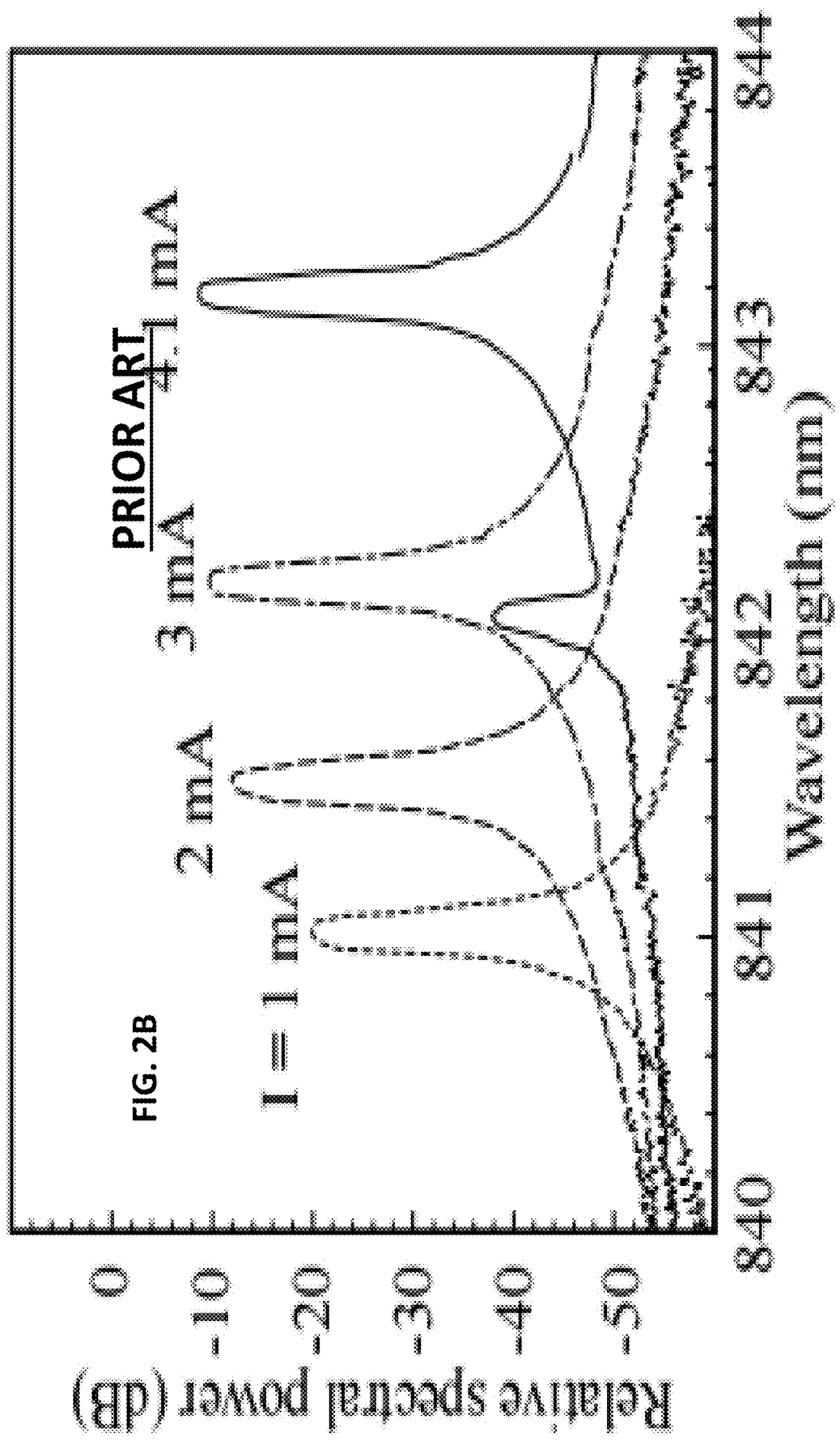
FIG. 2B (PRIOR ART) describes relative spectral power (dB) as a function of wavelength in one prior art example.
Figure 3:
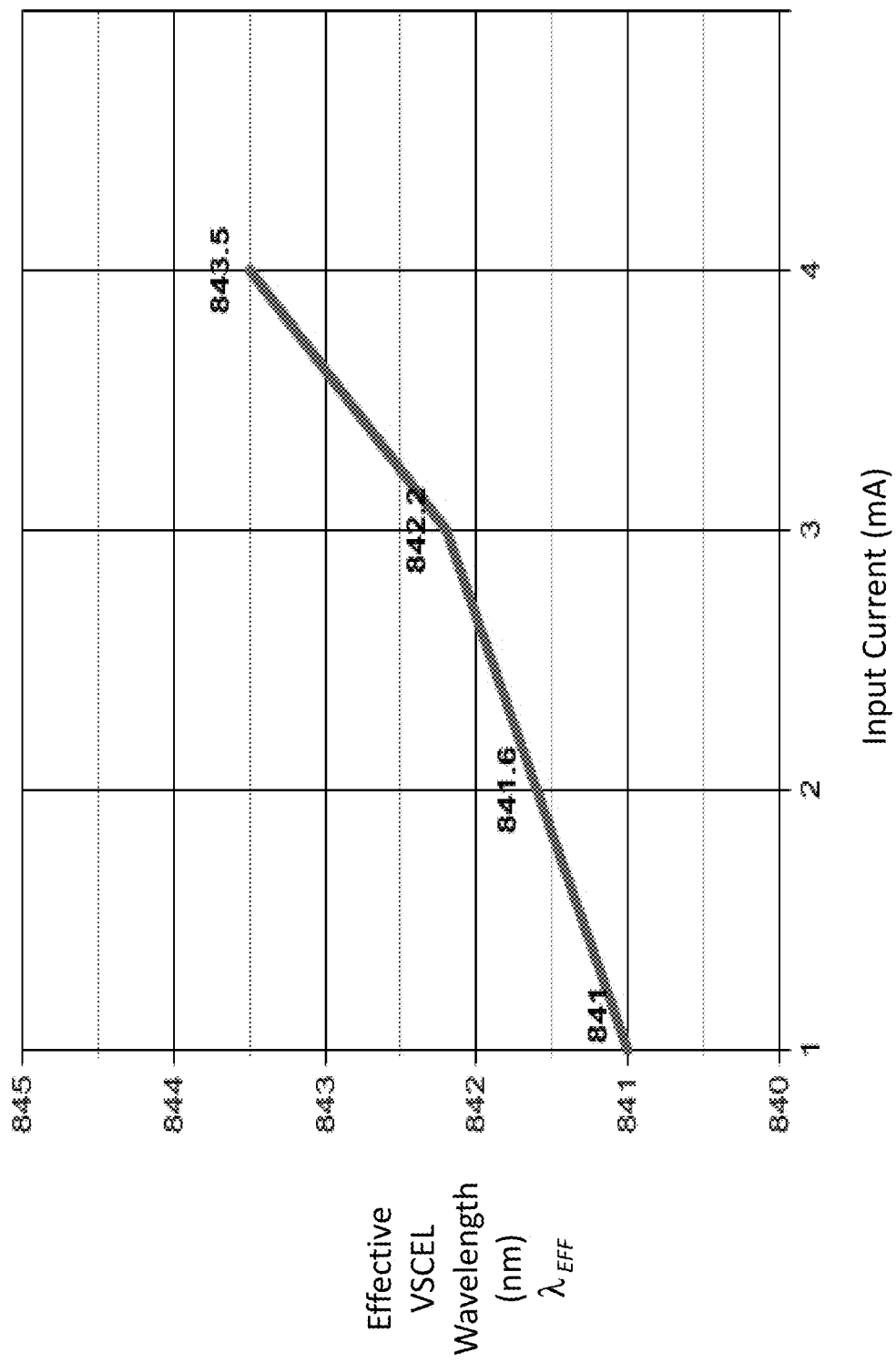
FIG. 3 describes relative spectral power (dB) as a function of wavelength in one example.

A Discussion of FIGS. 2A-2B and 3

Not wishing to be bound by theory, the wavelength of VCSEL is defined by the temperature of the junction. The temperature can be changed by manipulation of the current. For example, a single-mode VCSEL can be modulated with $\Delta\lambda/\Delta I=0.8$ nm/mA (300 GHz/mA). The red-shift of the emission spectra, with increasing current, indicates internal heating of the VCSEL. So the VCSEL wavelength can be tuned by sweeping its bias current, causing a rapid thermal effect that shifts the lasing wavelength.

FIG. 2A (PRIOR ART) illustrates a relative spectral power (Db) of a VSCEL (vertical-cavity surface-emitting laser) as a function of wavelength for one particular VSCEL when supplied with 2 mA of electrical current. Thus, although VSCELs are considered coherent sources of light, it is appreciated that not all light emitted by a VSCEL is at a single wavelength. Nevertheless, it is possible to characterize an effective wavelength of the VCSEL as the wavelength weighted by power (this can be defined as a ratio of integrals) the effective wavelength is typically close to but does not have to be exactly equal to the peak-power wavelength.

As shown in FIG. 2B (PRIOR ART), for VSCEL devices the effective wavelength as well as the peak-power wavelength depends as a function of input current supplied to the VCSEL—in the example of FIG. 2B, the greater the current supply, the greater the effective (as well as peak-power) wavelength. In the example of FIG. 2B, (i) when 1 mA of input current are supplied to the VCSEL, the peak-power wavelength is 841 nm, (ii) when 2 mA of input current are supplied to the VCSEL, the peak-power wavelength is 841.5 nm; (iii) when 3 mA of input current are supplied to the VCSEL, the peak-power wavelength is 842.3 nm, and (iv)

when 4 mA of input current are supplied to the VCSEL, the peak-power wavelength is 843.2 nm. This is also shown in FIG. 3.

Figure 6A:
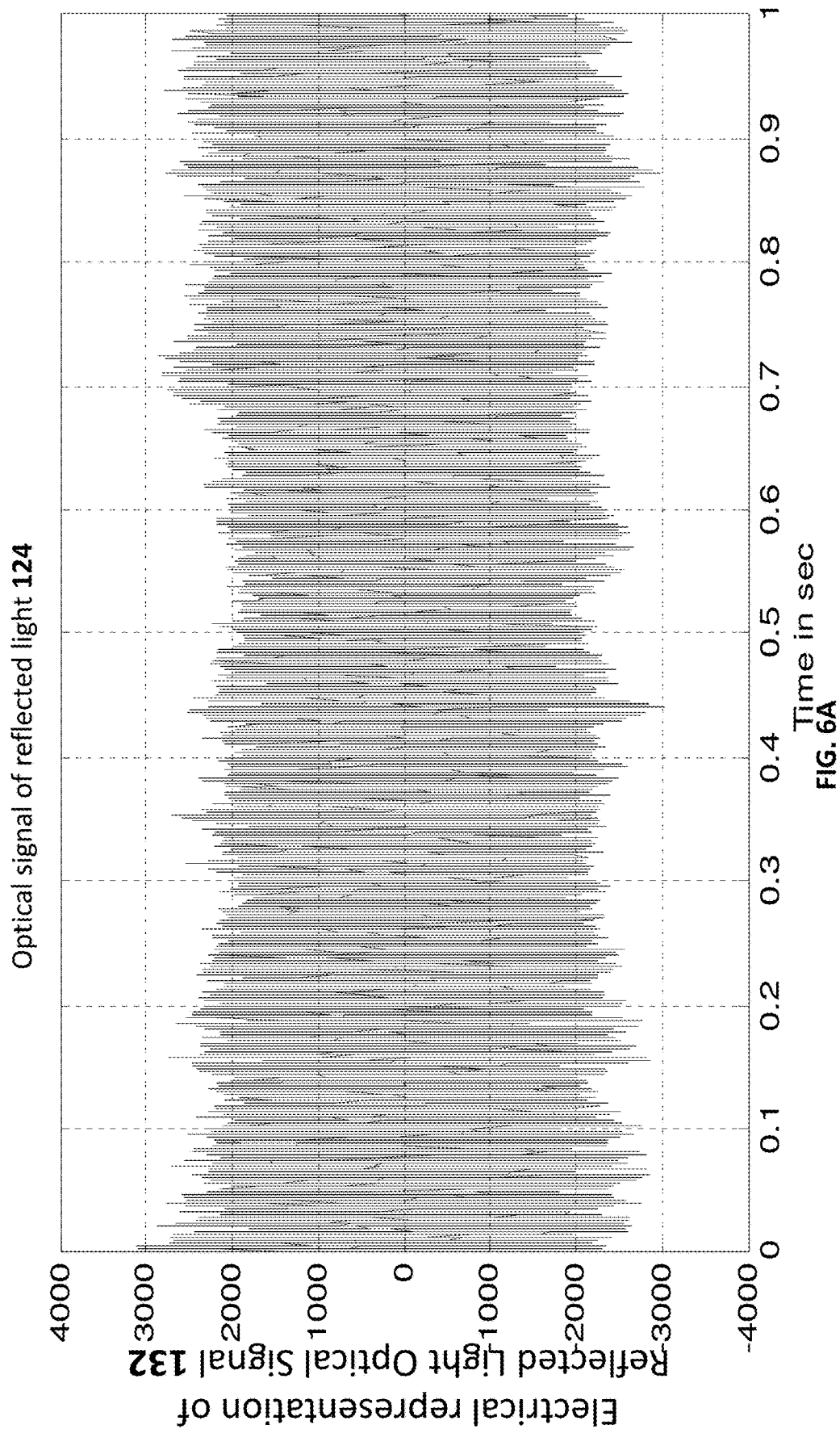
FIGS. 6A, 6B, 7, 8, and 9 show representations of reflected light optical signals according to different examples.
Figure 6B:
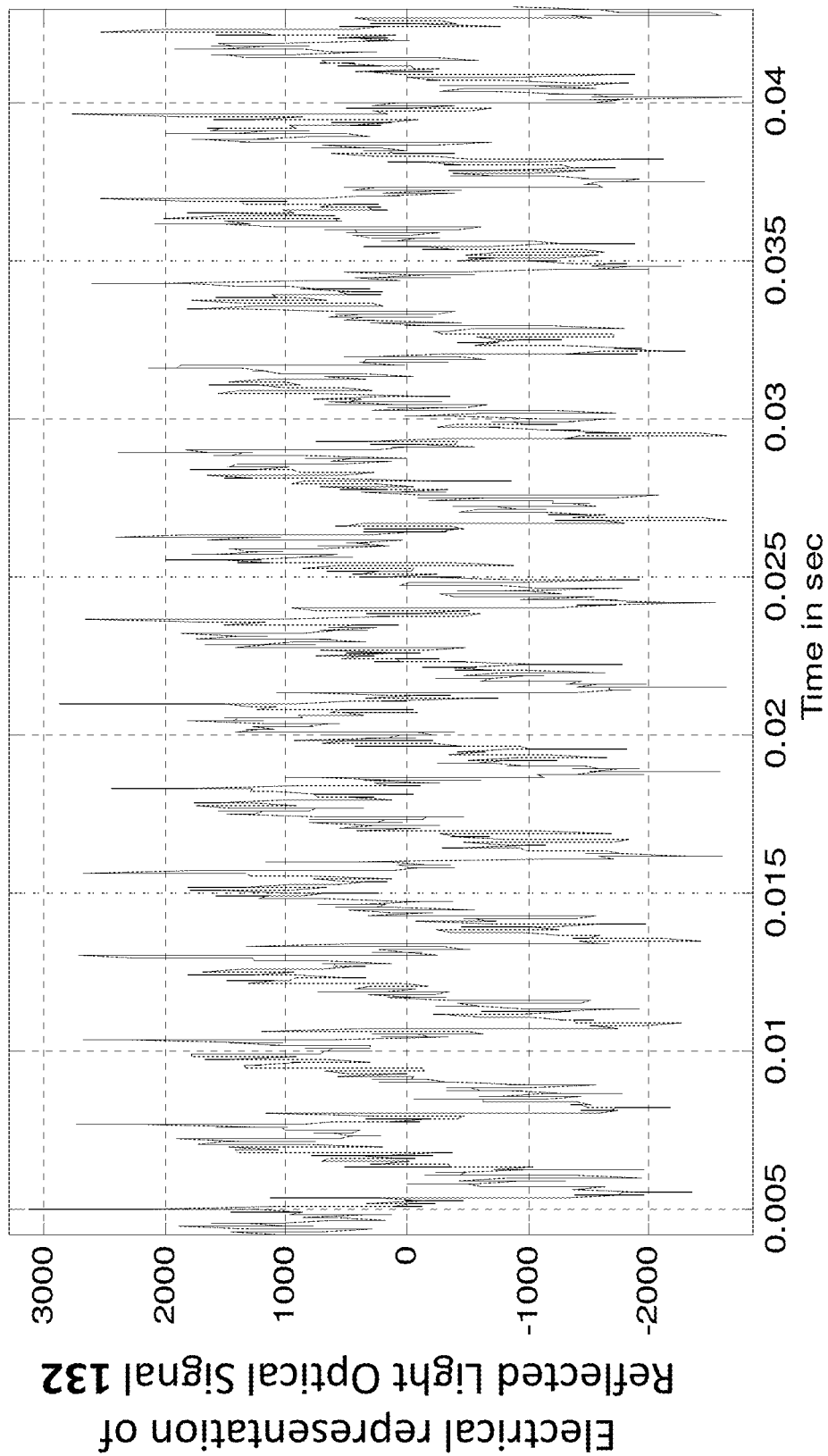
Figure 7:
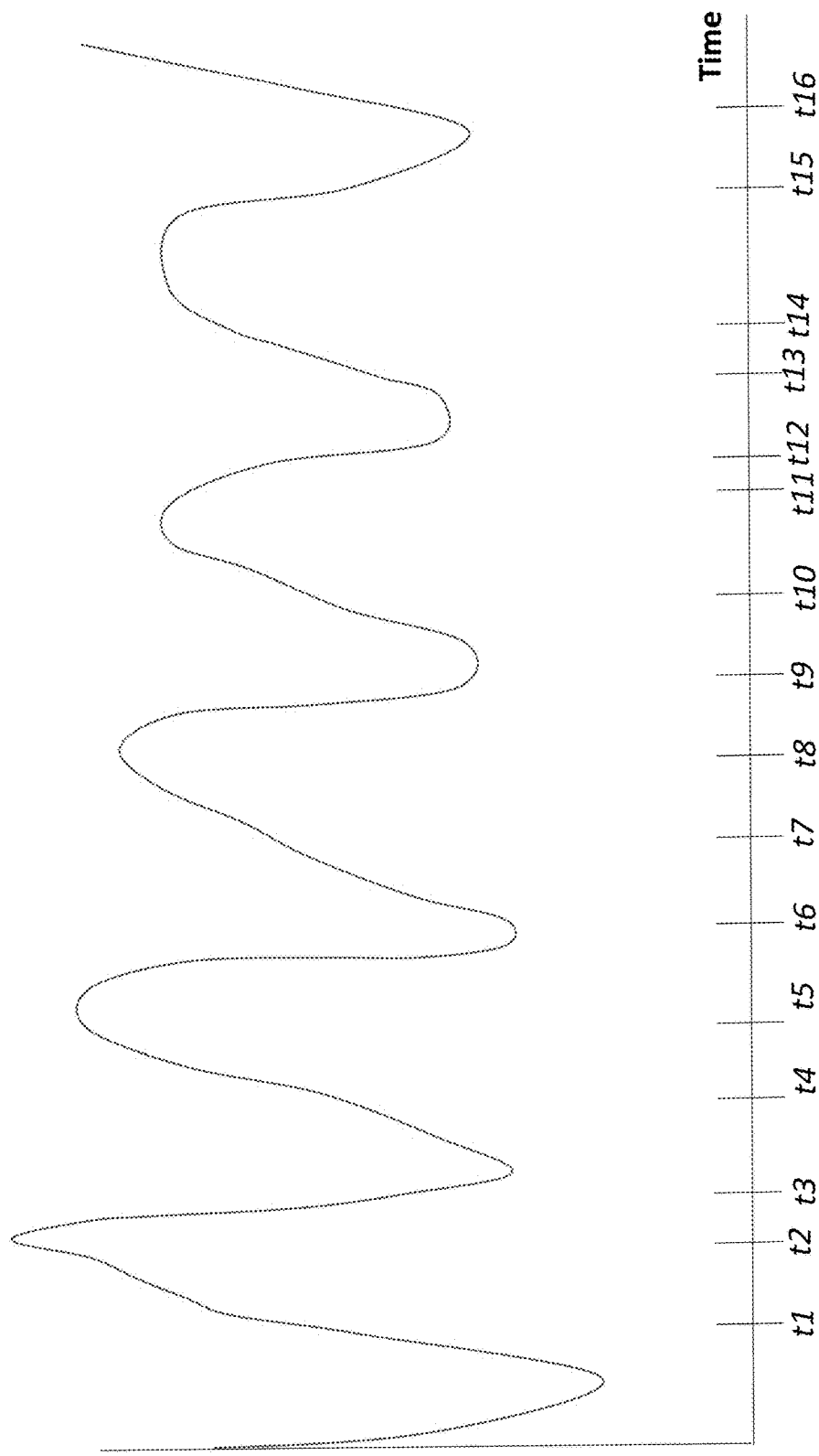
Figure 8:
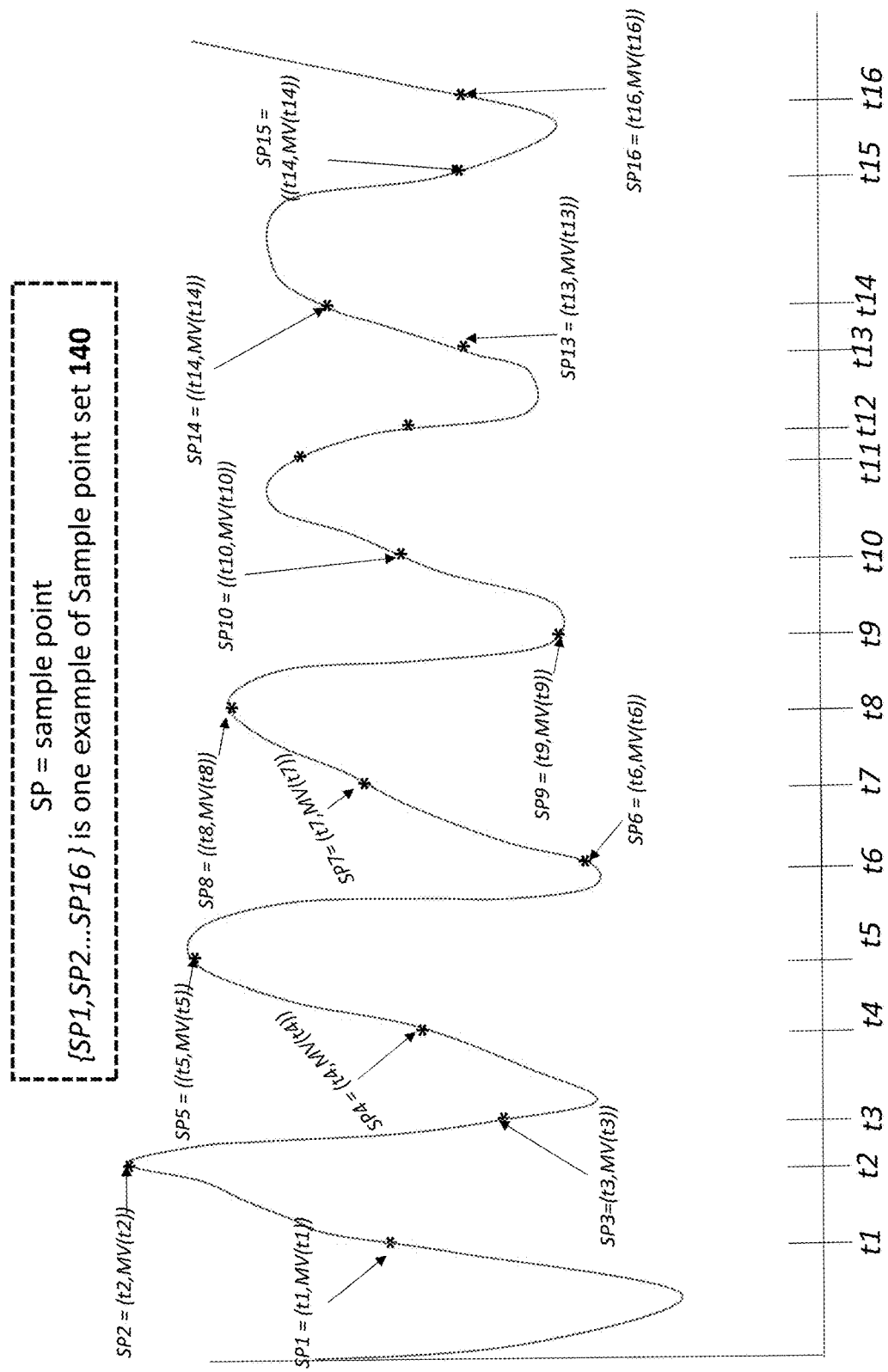

A Discussion of FIGS. 6-8

In some embodiments, it is possible to modulate the input current (see 112 of FIG. 1) supplied to VSCEL 114 as a function of time. One example is 'saw-tooth' modulation, as shown in FIG. 4—in one non-limiting example of I(t), a period of the saw-tooth is between 0.01 seconds and 0.2 seconds—for example, at least 0.03 seconds and/or at most 0.15 seconds.

Figure 4:
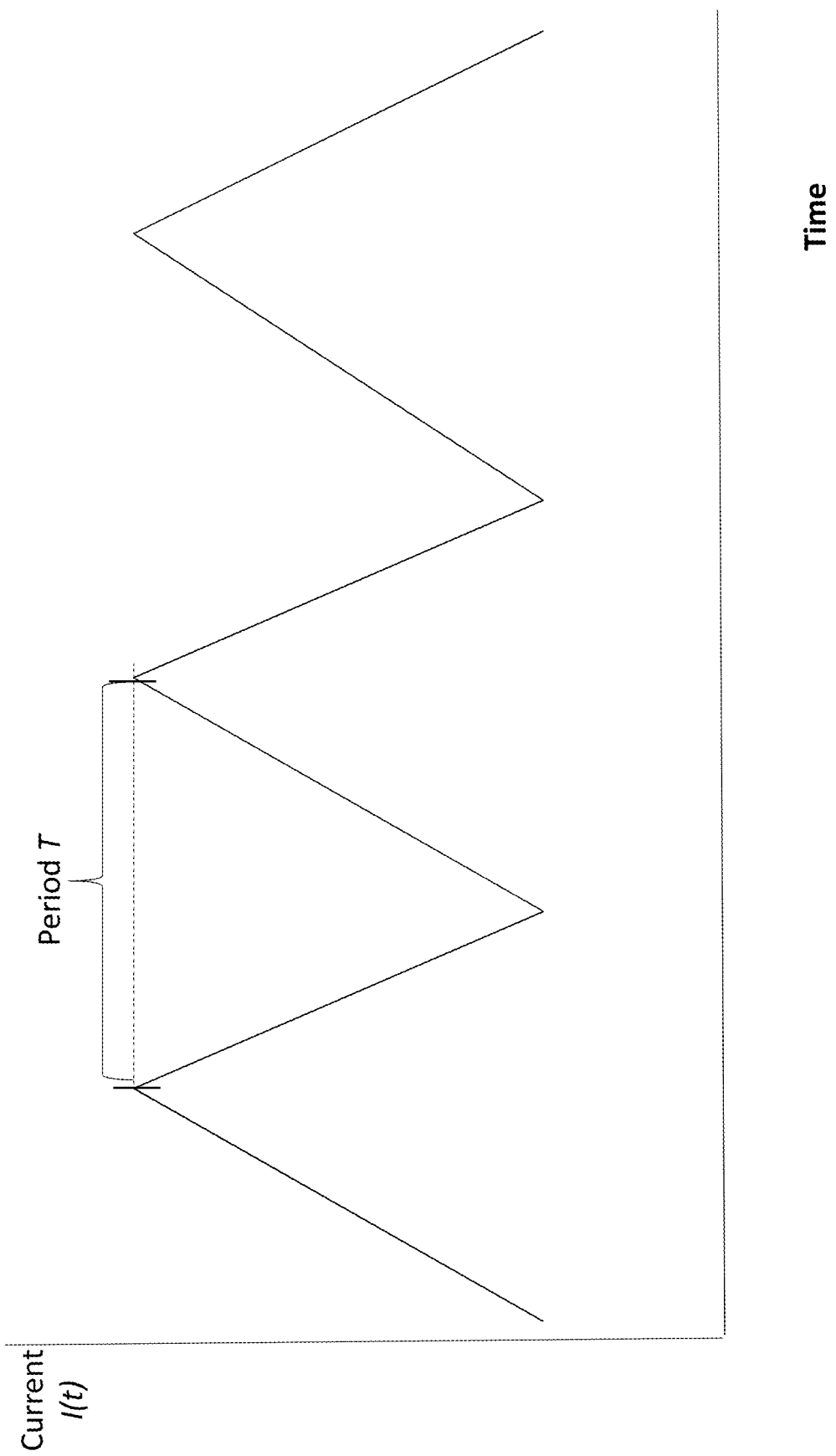
FIG. 4 illustrates one example of I(t) having a saw-tooth waveform.
Figure 5:
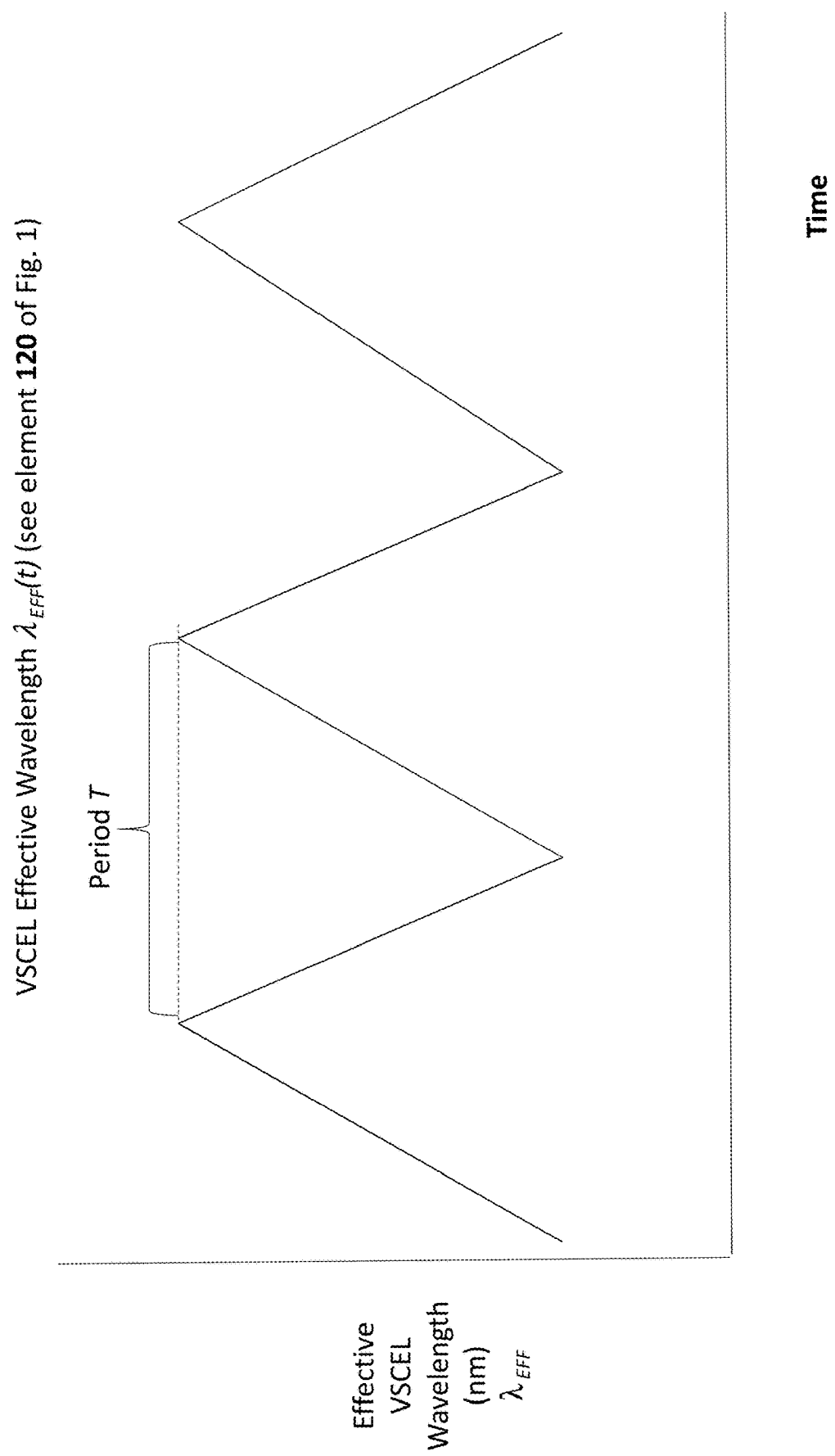
FIG. 5 illustrates a corresponding example of $\lambda_{EFF}(st_i)$ having the saw-tooth waveform.

FIG. 5 illustrates $\lambda_{EFF}(t)$, according to one particular VCSEL that is supplied with input current I(t) according to the example of FIG. 4.

Referring once again to FIG. 1, it is noted that upon reflection from skin 116 (FIG. 1A where the skin includes blood vessels where blood flows therein) or from fluid 216, reflected light 124 is received by detector 128. This reflected light includes a reflected light optical signal, a representation 132 of which is generated by detector 128 (e.g. comprising any photodetector(s) including but not limited to silicon-based detectors, CMOS detectors, and CCDs). One example of an electrical representation 132 the reflected light optical signal is shown in FIGS. 6A-6B where the time-scales are different.

Both FIGS. 6 and 7 are illustrative example of an electrical representation 132 the reflected light optical signal—however, FIG. 7 is an artificial example manually generated and presented for heuristics. FIG. 8 illustrates sampling of electrical representation 132 the reflected light optical signal for 16 sample-times t1, t2 . . . t16 to generate a set 140 16 sample points {(t1,MV(t1),(t2,MV(t2), . . . {(t16,MV(t16),} where: (i) $st_1$ is t1, $st_2$ is t2 and so on and (ii) MV(t1) is the measurement value at ti (and hence at $st_i$) and is the value of the curve 132 at sample-time ti.

Figure 10:
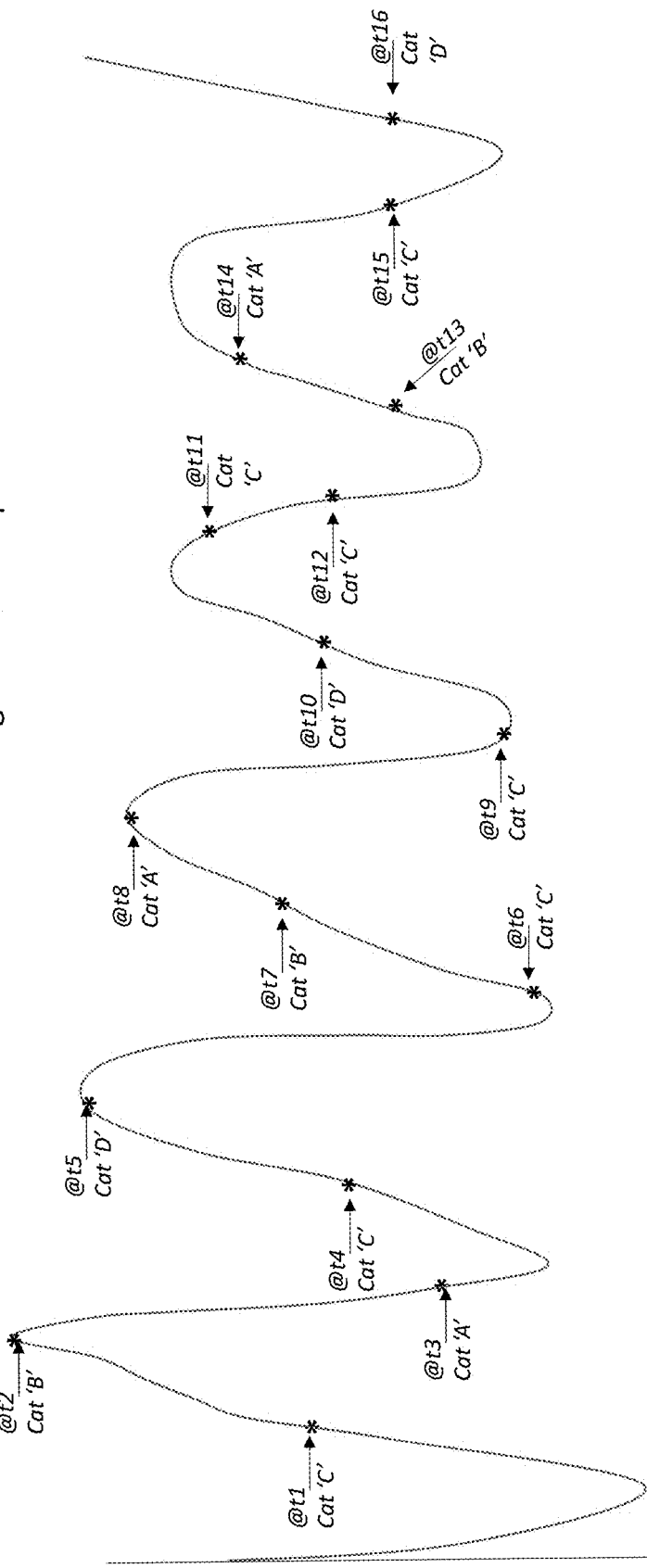
FIG. 10 illustrates categorization of the 16 sample points of FIG. 8 according to the categorization of the example of FIG. 9.

A Discussion of FIGS. 9-11

Embodiments of the present invention relate to controlling $\lambda_{EFF}(t)$ to create multiple 'ensembles' of stochastically-moving particles (e.g. micro-particles RBCs) suspended within a fluid (e.g. blood plasma).

Towards this end, it is useful to categorize sample points of set 140 according (i) to the sample time st, of each sample point and (ii) in particular, according to $\lambda_{EFF}(st_i)$ for each sample point $(st_i,MV(st_i))$.

FIG. 9 illustrates the same function $\lambda_{EFF}(t)$ illustrated in FIG. 5. Superimposed on the graph of FIG. 9 are the sample times t1, t2 . . . t16 appearing in FIG. 8. Also illustrated in FIG. 9 are four wavelength ranges $R_1$, $R_2$, $R_3$ and $R_4$. The categorization of sample-points according to the example of FIG. 9 is as follows: for each sample point $SP=(st_i,MV(st_i))$, (i) if $\lambda_{EFF}(st_i)$ is within wavelength range $R_1$, then the sample point SP (as well as its sample time $st_i$) is classified by classifier 144 into 'category A,' (ii) otherwise, if $\lambda_{EFF}(st_i)$ is within wavelength range $R_2$, then the sample point SP (as well as its sample time $st_i$) is classified by classifier 144 into 'category B,' (iii) otherwise, if $\lambda_{EFF}(st_i)$ is within wavelength range $R_3$, then the sample point SP (as well as its sample time $st_i$) is classified by classifier 144 into 'category C,' (iv) otherwise, if $\lambda_{EFF}(st_i)$ is within wavelength range $R_4$, then the sample point SP (as well as its sample time $st_i$) is classified by classifier 144 into 'category D'.

There are 4 categories in FIG. 9 thus, Q=4 in this example.

FIG. 10 illustrates categorization of the 16 sample points of FIG. 8 according to the categorization of the example of FIG. 9. Thus, the first sample point SP1=(t1,MV(t1)) is in category 'C', the second sample point SP1=(t1,MV(t1)) is in category 'B',and so on.

Figure 11D:
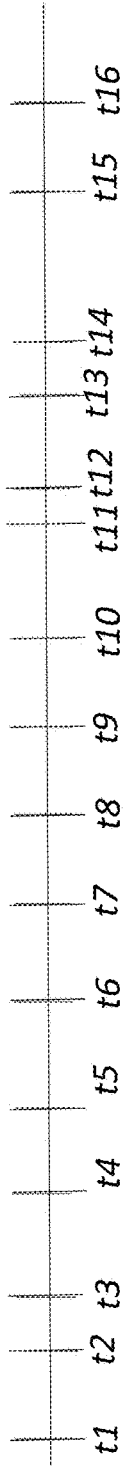
FIG. 11D illustrates the sample points of the sample set of FIG. 8 that are categorized into 'category D.'

FIG. 11A illustrates the sample points of the sample set of FIG. 8 that are categorized into 'category A' (and thus is one example of set 148[1]); FIG. 11B illustrates the sample points of the sample set of FIG. 8 that are categorized into 'category B' (and thus is one example of set 148[2]); FIG. 11C illustrates the sample points of the sample set of FIG. 8 that are categorized into 'category C' (and thus is one example of set 148[3]); FIG. 11D illustrates the sample points of the sample set of FIG. 8 that are categorized into 'category D' (and thus is one example of set 148[4]).

Figure 12:
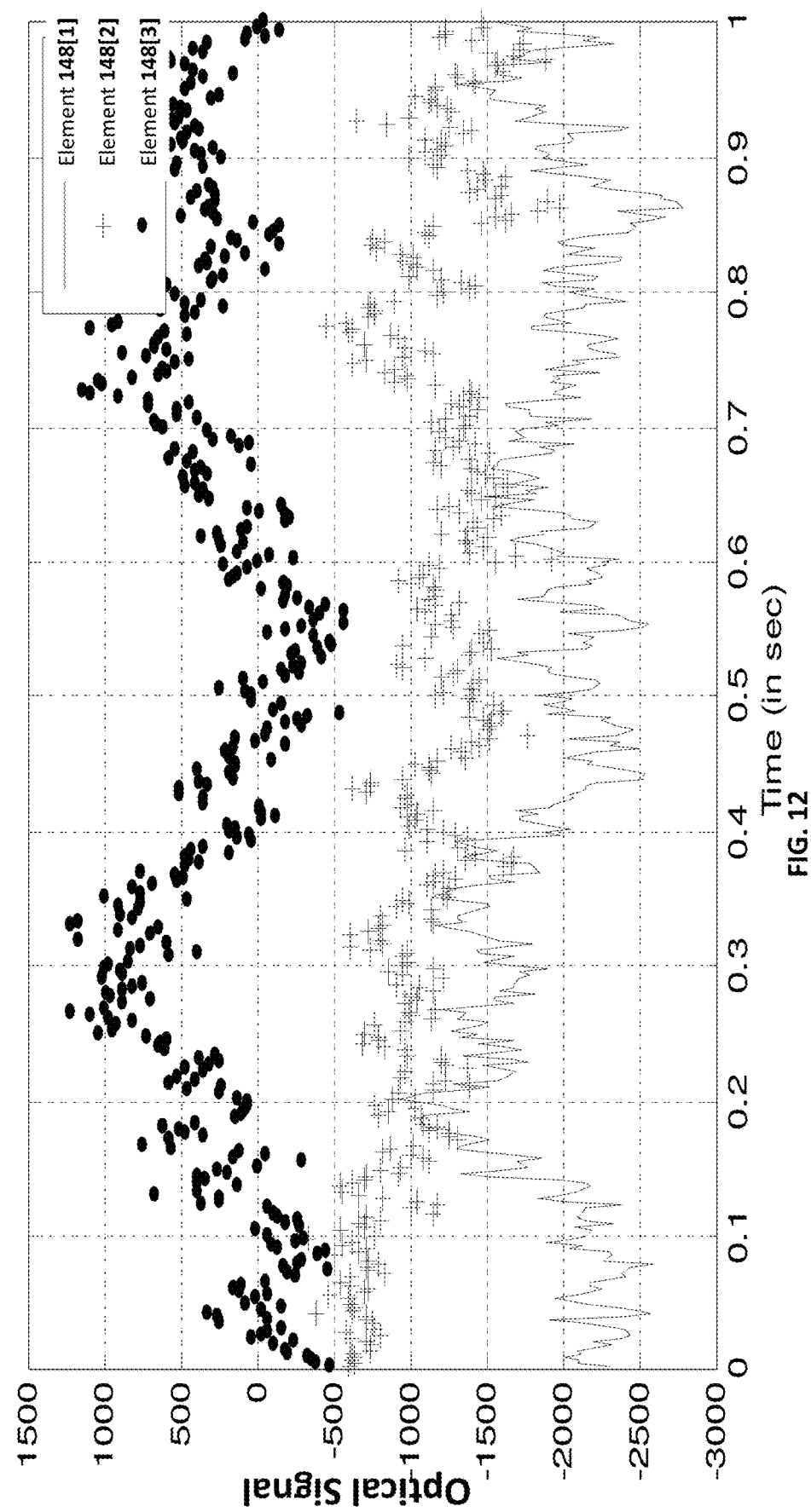
FIG. 12 is an illustration of 148[1]-148[3] for the example FIGS. 6A-6B.
Figure 13:
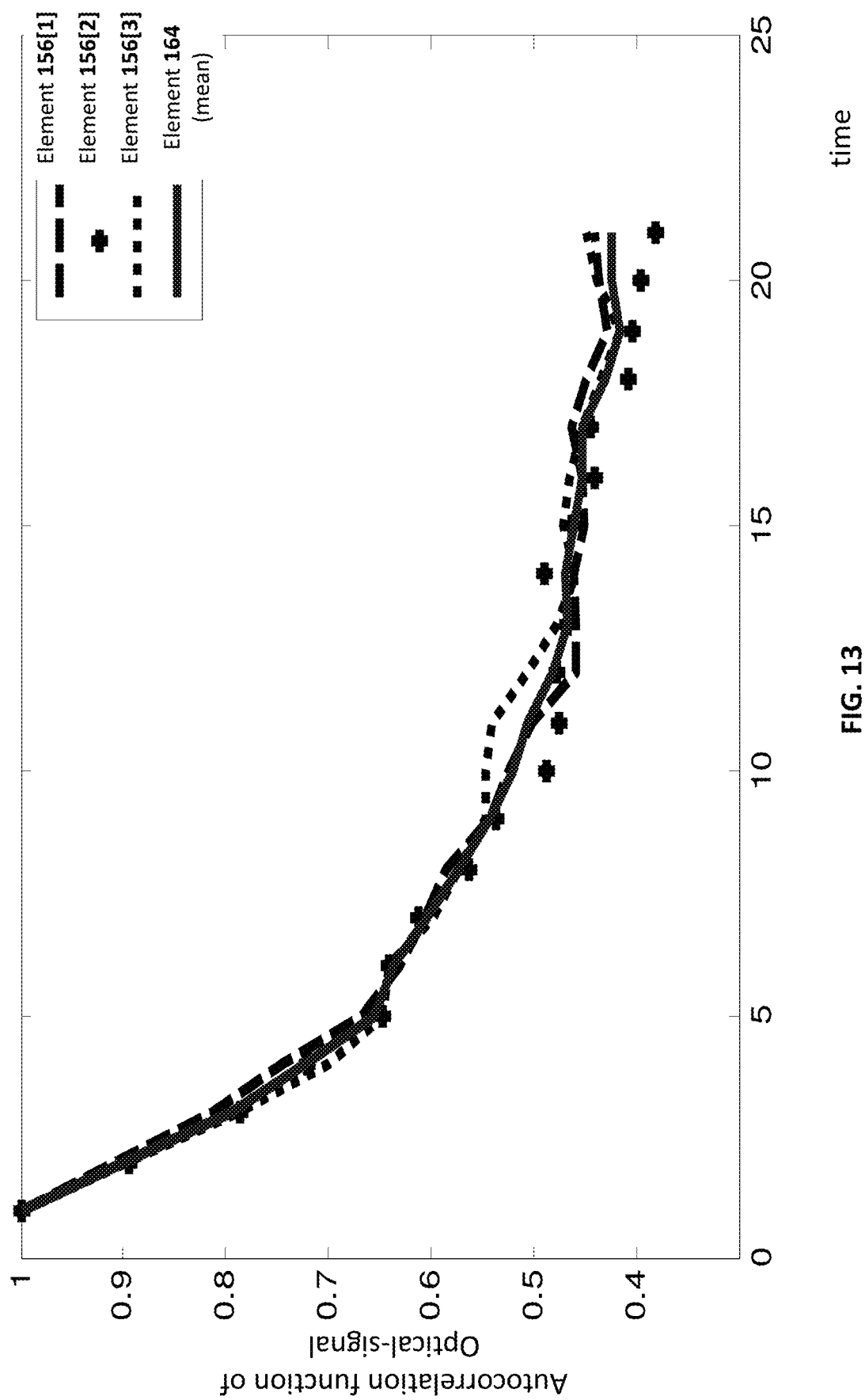
FIG. 13 illustrate the 156[1]-156[3] corresponding to 148[1]-148[3] of FIG. 12.
Figure 14:
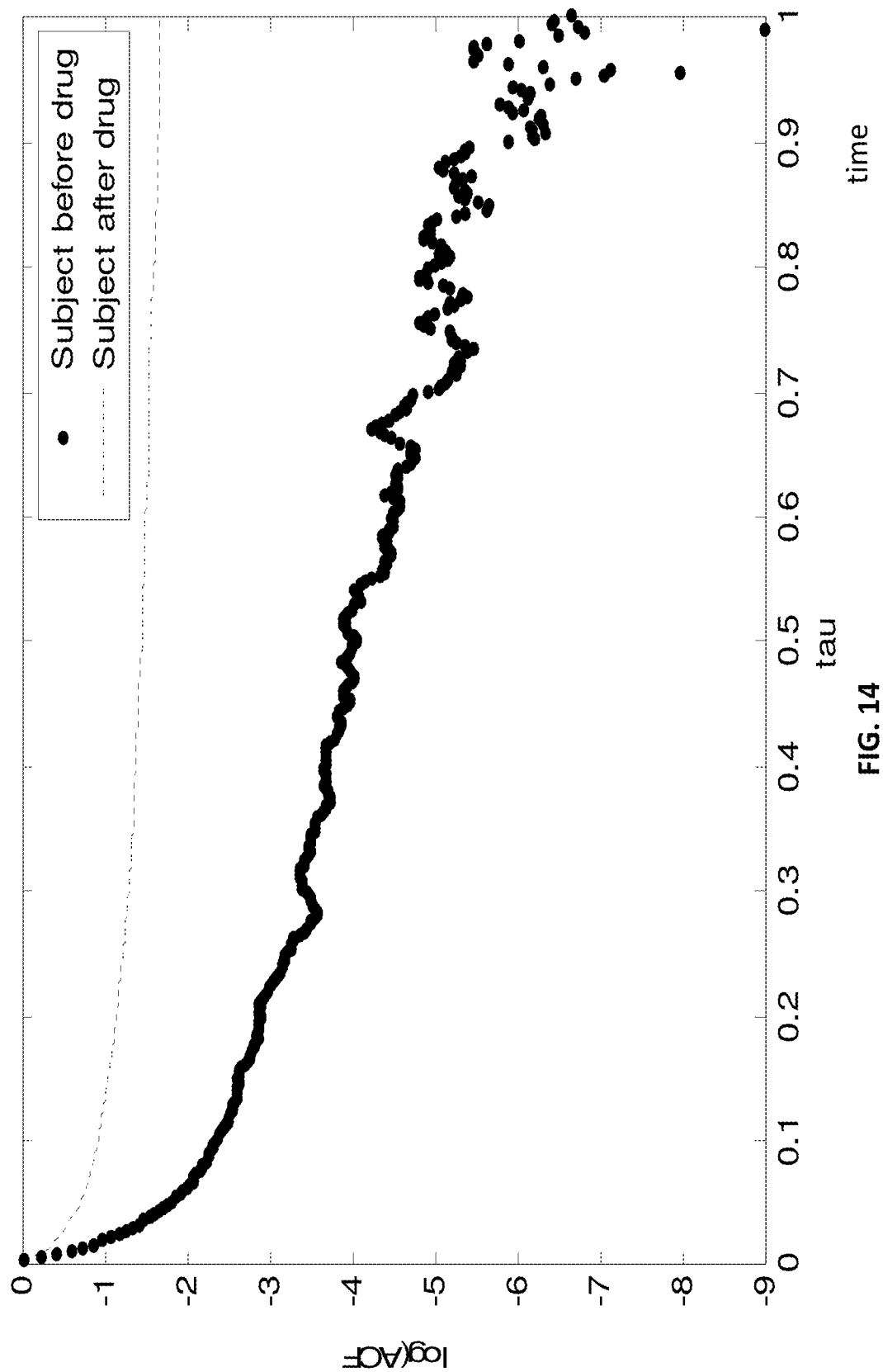
FIG. 14 illustrates plots examples of the log of the autrocorrelation function versus tau for (i) subject before drug and (ii) subject after drug.

Discussion of FIGS. 12-14

Figure 17:
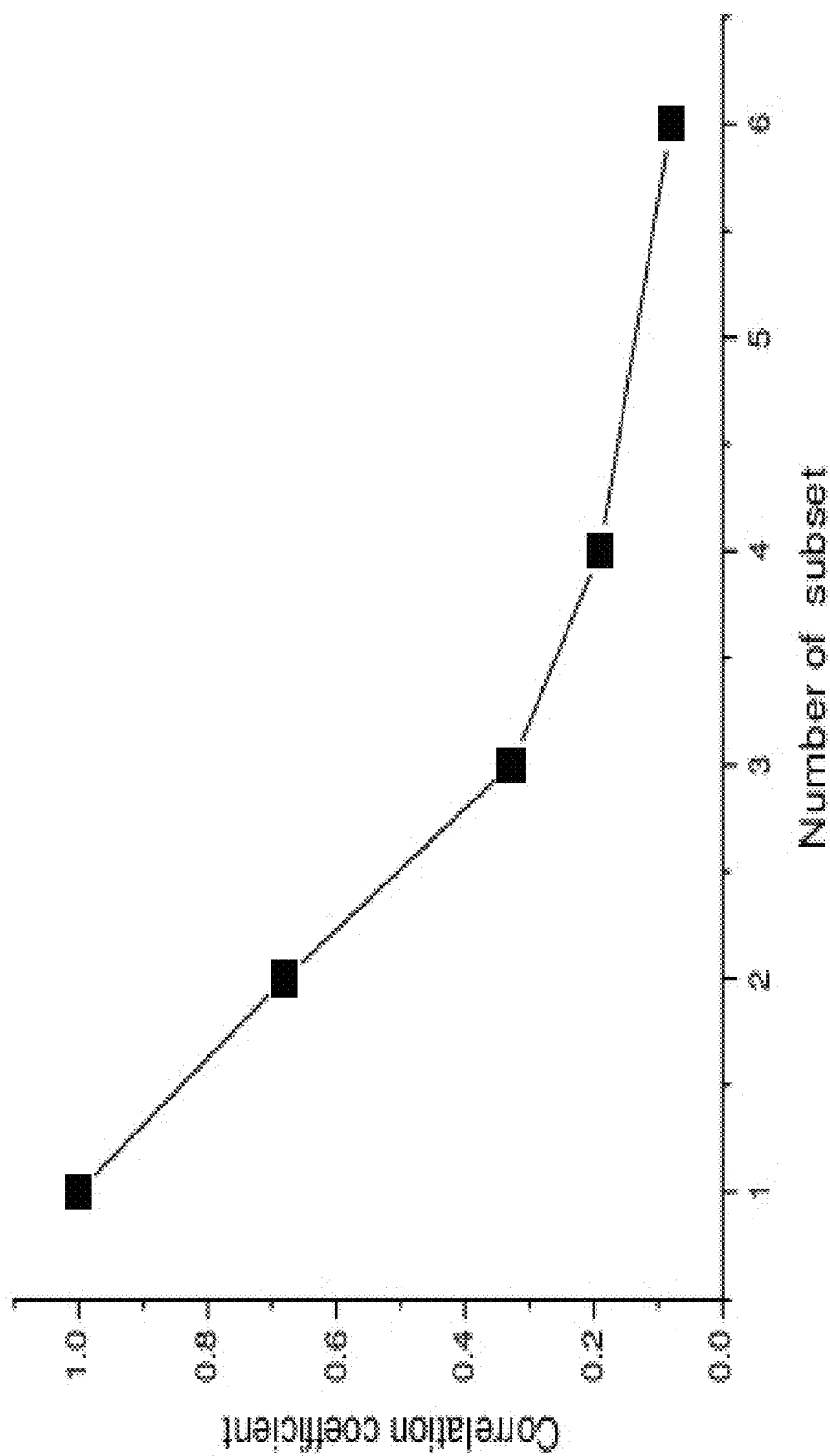
FIG. 17 illustrates a relation between the correlation coefficient as a function of the number of subsets.

FIG. 12 is an illustration of 148[1]-148[3] for the example FIGS. 6A-6B. As shown in FIG. 12, the data sets are not well correlated with each other. FIG. 17 is another example, where data-sets are marked 1, 2, 3, 4, 5 and 6 data set '1' is well correlated with itself but not well correlated with data set '6'. In different embodiments, the sets 148 are formed from 140 so that for each i,j where i≠j, the cross-correlation between 148[i] and 148[j] is at most 0.4 or at most 0.3 or at most 0.2 or at most 0.1.

In different embodiments, a cardinality of each of the sets 148 is at least 10 or at least 20 or at least 50 or at least 100. In different embodiments, each of the sets 148 includes sampling times (at least 1 or at least 2 or at least 3 or at least 5 per second) for at least 1 second or at least 2 seconds or at least 3 seconds or at least 5 seconds or at least 10 seconds or at least 20 seconds or at least 30 seconds or at least 1 minute or at least 2 minutes.

As noted above, each of 148[i] is processed by 152 to generate a respective 156[i]. Thus, FIG. 13 illustrate the 156[1]-156[3] corresponding to 148[1]-148[3] of FIG. 12.

Also illustrated in FIG. 13 is the average of 156[1]-156[3], which is 164 (i.e. generated by 160) which is clearly 'smoother' than any of the 156[i].

Figure 15A:
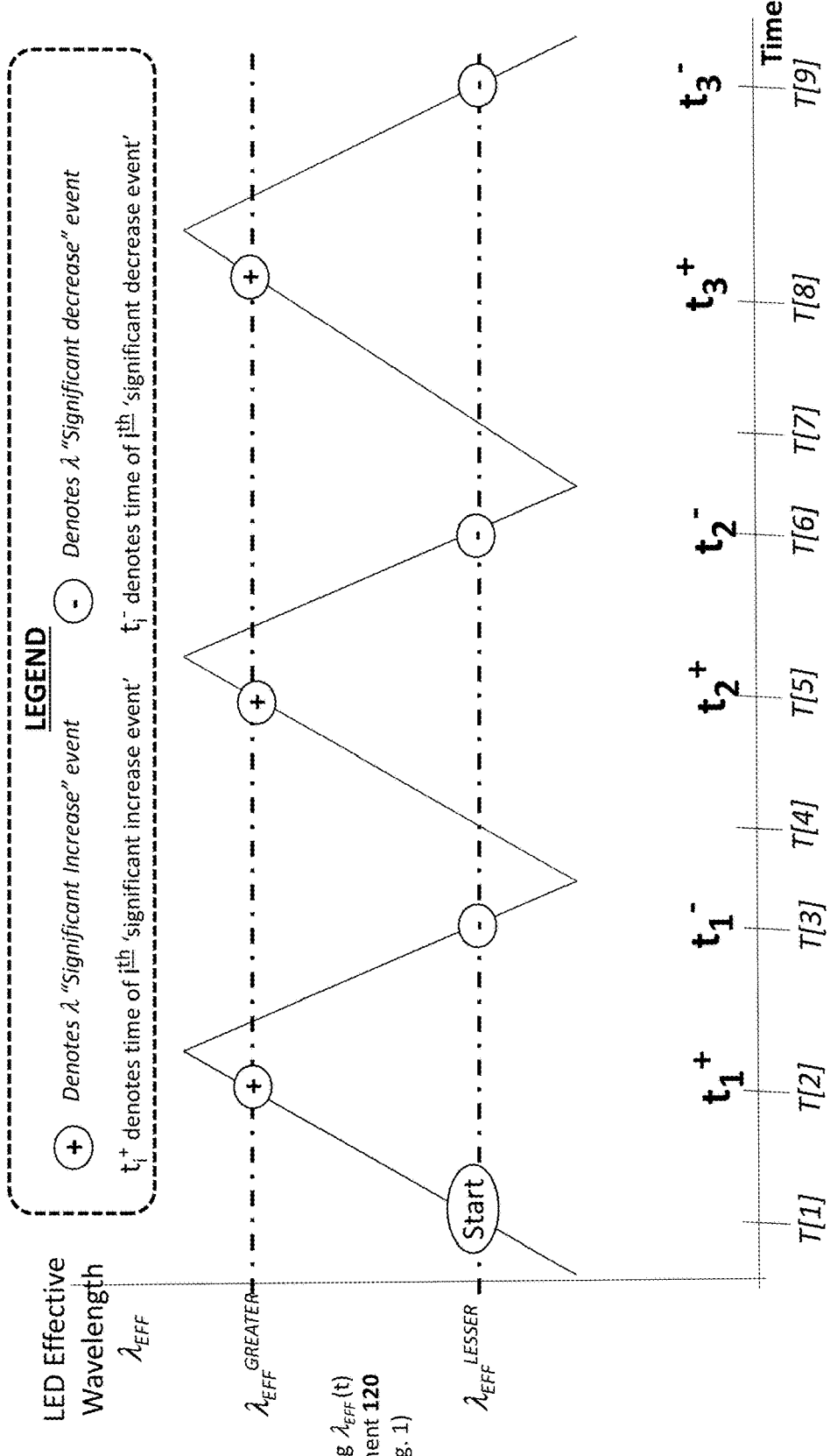
FIGS. 15A-15B graph the time-dependence of LED effective wavelength for two examples.
Figure 15B:
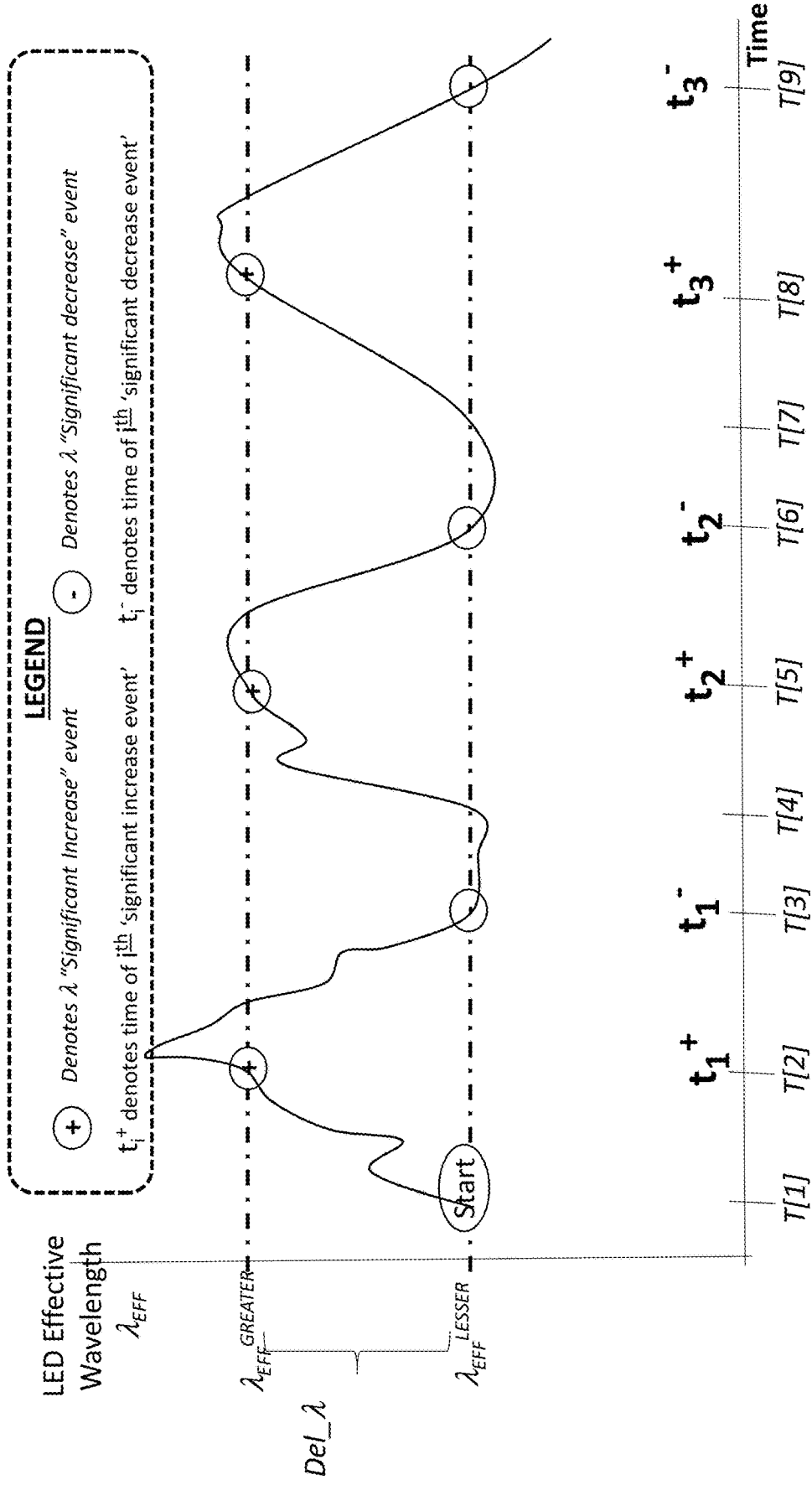
Figure 16:
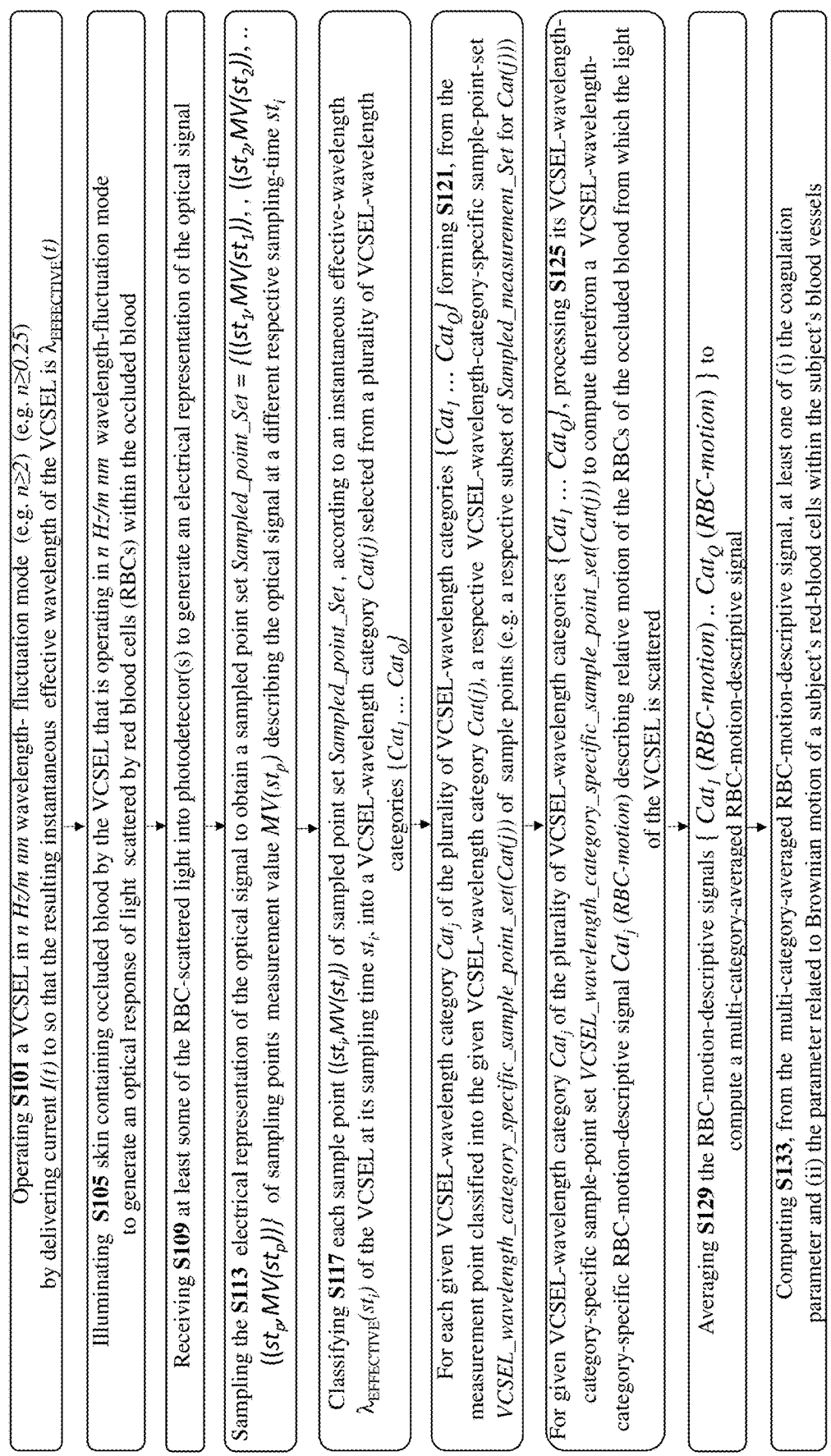
FIG. 16 is a flow-chart describing a technique for computing at a coagulation parameter and/or a parameter related to Brownian motion.

Discussion of FIGS. 15A-15B a Discussion of a Wavelength-Decrease Events

As discussed above, the input current I provided to VCSEL 114 varies in time as I(t) in order to cause the effective wavelength of light 120 emitted by VCSEL 114 to vary according to $\lambda_{EFF}(st_i)$. FIG. 4 illustrates one example of I(t) having a saw-tooth waveform; FIG. 5 illustrates a corresponding example of $\lambda_{EFF}(st_i)$ also having the saw-tooth waveform. FIG. 15A has the same saw-tooth waveform; however, as illustrated in FIG. 15B the saw-tooth waveform.

For the present disclosure, an wavelength increase-decrease event is (i) an increase in an effective wavelength of the VCSEL of at least m nm is (ii) followed by a decrease of the effective wavelength of the VCSEL of at least m nm. In the example of FIG. 15A, m=Del_λ (this is $\lambda_{EFF}^{GREATER}-\lambda_{EFF}^{LESSER}$) and there are 3 wavelength increase-decrease event illustrated—(i) a first event including an increase portion (concluding at T[2] and marked by $t_1^+$) and a decrease portion (concluding at T[3] and marked by $t_1^-$)—overall the first event begins at T[1] and concludes at T[3]); (ii) a second event including an increase portion (concluding at T[5] and marked by $t_2^+$) and a decrease portion (concluding at T[6] and marked by $t_2^-$)—overall the second event begins at T[4] and concludes at T[6]);

(iii) a third event including an increase portion (concluding at T[8] and marked by $t_3^+$) and a decrease portion (concluding at T[9] and marked by t3) overall the second event begins at T[7] and concludes at T[9]).

First Additional Discussion

An in-vivo method for measuring at least one blood parameter, the method comprising:

a. operating (e.g. S101) a VCSEL in n Hz/m nm wavelength-fluctuation mode (n≥2) by varying an amount of electrical current delivered to the VCSEL to cause at least n distinct m nm wavelength-increase-decrease events per second where for each wavelength-increase-decrease event, an increase in an effective wavelength of the VCSEL of at least m nm is followed by a decrease of the effective wavelength of the VCSEL of at least m nm, a value of n being at least 2 (e.g. at least 3 or at least 5 or at least 10 or at least 20 or at least 50) and a value of m being at least 0.25 or at least 0.5 or at least 0.75 or at least 1, the time-dependence of an instantaneous amount of current defining a function I(t), the time-dependence of an instantaneous effective wavelength of the VCSEL being $\lambda_{EFFECTIVE}(t)$;

b. illuminating (e.g. S105) skin containing occluded blood by the VCSEL that is operating in n Hz/m nm wavelength-fluctuation mode to generate an optical response of light scattered by red blood cells (RBCs) within the occluded blood;

c. receiving (e.g. S109) at least some of the RBC-scattered light into photodetector(s) to generate an electrical representation of the optical signal; and d. sampling (e.g. S113) the electrical representation of the optical signal to obtain a sample point set Sample_Point_Set={$(st_1, MV(st_1)), (st_2, MV(st_2)), \ldots (st_P, MV(st_P))$,} of sample points, each sample point $(st_i, MV(st_i))$ being an ordered pair where measurement value $MV(st_i)$ describes the optical signal at a different respective sampling-time $st_i$;

e. classifying (e.g. S117) each sample point $(st_i, MV(st_i))$ of the sample point set Sample_Point_Set, according to an instantaneous effective-wavelength $\lambda_{EFFECTIVE}(st_i)$ of the VCSEL at its sampling time $st_i$, into a VCSEL-wavelength category Cat(j) selected from a plurality of VCSEL-wavelength categories {$Cat_1 \ldots Cat_Q$};

f. for each given VCSEL-wavelength category $Cat_j$ of the plurality of VCSEL-wavelength categories {$Cat_1 \ldots Cat_Q$} forming (e.g. S121), from the sample points classified into the given VCSEL-wavelength category Cat(j), a respective VCSEL-wavelength-category-specific sample point set VCSEL_wavelength_specific_sample_points(Cat(j)) of sample points {$(st_{1\_CAT(j)}, MV(st_{1\_CAT(j)})),(st_{2\_CAT(j)}, MV(st_{2\_CAT(j)})), \ldots$ } g. for each given VCSEL-wavelength category $Cat_j$ of the plurality of VCSEL-wavelength categories {$Cat_1 \ldots Cat_Q$}, processing (e.g. S125) its VCSEL-wavelength-category-specific sample point set VCSEL_wavelength_specific_sample_points(Cat(j)) to compute therefrom a VCSEL-wavelength-category-specific RBC-motion-descriptive signal $Cat_j$ (RBC-motion) describing relative motion of the RBCs of the occluded blood from which the light of the VCSEL is scattered;

i. averaging (e.g. S129) the RBC-motion-descriptive signals {$Cat_1$ (RBC-motion) ... $Cat_Q$ (RBC-motion)} to compute a multi-category-averaged RBC-motion-descriptive signal; and j. computing (e.g. S133) the blood parameter from the multi-category-averaged RBC-motion-descriptive signal.

An in-vivo method for measuring at least one blood parameter, the method comprising:

a. supplying a time-fluctuating input current to a VCSEL to modulate a VCSEL output-wavelength according to VSCEL output-wavelength temporal-modulation-pattern;

b. illuminating skin containing occluded blood by the VCSEL to generate an optical response of light scattered by red blood cells (RBCs) within the occluded blood;

c. receiving at least some of the RBC-scattered light into photodetector(s); and d. analyzing, in accordance with the VSCEL output-wavelength temporal-modulation-pattern, an electrical representation of the optical signal as derived from output of the photodetector(s) so as to compute the blood parameter.

In some embodiments, VCSEL is operated in n Hz/m nm wavelength-fluctuation mode (n≥2) by varying an amount of electrical current delivered to the VCSEL to cause at least n distinct m nm wavelength-increase-decrease events per second where for each wavelength-increase-decrease event, an increase in an effective wavelength of the VCSEL of at least m nm is followed by a decrease of the effective wavelength of the VCSEL of at least m nm, a value of n being at least 2 (e.g. at least 3 or at least 5 or at least 10 or at least 20 or at least 50) and a value of m being at least 0.25 or at least 0.5 or at least 0.75 or at least 1, the time-dependence of an instantaneous amount of current defining a function I(t), the time-dependence of an instantaneous effective wavelength of the VCSEL being $\lambda_{EFFECTIVE}(t)$.

In some embodiments, the blood parameter is selected from the group consisting of a blood plasma viscosity, an RBC diffusion coefficient, and a coagulation parameter.

In some embodiments, the parameter describes Brownian motion of a subject's red-blood cells within the subject's blood vessels.

In some embodiments, the skin is illuminated at a blood-flow restriction-location and the skin is illuminated downstream of the blood-flow restriction-location.

In some embodiments, the analysis of the electrical representation of the optical signal as derived from output of the photodetector(s) and/or the computing of the RBC-motion-descriptive signals comprises computing at least the following functions of the sample-set-specific optical-response-descriptive electrical signals: (i) an autocorrelation function (ACF), (ii) a Hurst function; (iii) a fractal dimension; and (iv) an entropy.

A method for measuring at least one parameter that is (i) descriptive of stochastic motion of suspended particles within a fluid; and/or (ii) is a rheological property of the fluid or of the suspension; (iii) describes a concentration of suspended particles within the fluid; and/or (iv) is a diffusion coefficient of the suspended particles and/or (iv) is a viscosity of the fluid or of the suspension; and/or (v) is a food aging or spoilage parameter and/or (vii) is an in-vivo or in-vitro blood coagulation parameter, the method comprising:

a. operating a VCSEL in n Hz/m nm wavelength-fluctuation mode (n≥2) by varying an amount of electrical current delivered to the VCSEL to cause at least n distinct m nm wavelength-increase-decrease events per second where for each wavelength-increase-decrease event, an increase in an effective wavelength of the VCSEL of at least m nm is followed by a decrease of the effective wavelength of the VCSEL of at least m nm, a value of n being at least 2 (e.g. at least 3 or at least 5 or at least 10 or at least 20 or at least 50) and a value of m being at least 0.25 or at least 0.5 or at least 0.75 or at least 1, the time-dependence of an instantaneous amount of current defining a function I(t), the time-dependence of an instantaneous effective wavelength of the VCSEL being $\lambda_{EFFECTIVE}(t)$;

b. illuminating the moving particles within the fluid by the VCSEL that is operating in n Hz/m nm wavelength-fluctuation mode to generate an optical response of light scattered by the suspended and moving particles within the fluid;

c. receiving at least some of the particle-scattered light into photodetector(s) to generate an electrical representation of the optical signal; and d. sampling the electrical representation of the optical signal to obtain a sample point set Sample_Point_Set={ $(st_1, MV(st_1)), (st_2, MV(st_2)),) \ldots (st_P, MV(st_P)),$} of sample points, each sample point $(st_i, MV(st_i)$ being an ordered pair where measurement value $MV(st_i)$ describes the optical signal at a different respective sampling-time $st_i$;

e. classifying each sample point $(st_i, MV(st_i)$ of the sample point set Sampled_point_Set, according to an instantaneous effective-wavelength $\lambda_{EFFECTIVE}(st_i)$ of the VCSEL at its sampling time $st_i$, into a VCSEL-wavelength category Cat(j) selected from a plurality of VCSEL-wavelength categories {$Cat_1 \ldots Cat_Q$};

f. for each given VCSEL-wavelength category $Cat_j$ of the plurality of VCSEL-wavelength categories {$Cat_1 \ldots Cat_Q$} forming, from the sample points classified into the given VCSEL-wavelength category Cat(j), a respective VCSEL-wavelength-category-specific sample point set VCSEL_wavelength_specific_sample_points(Cat(j)) of sample points {$(st_{1\_CAT(j)}, MV(st_{1\_CAT(j)})),(st_{2\_CAT(j)}, MV(st_{2\_CAT(j)}), \ldots$} g. for each given VCSEL-wavelength category $Cat_j$ of the plurality of VCSEL-wavelength categories {$Cat_1 \ldots Cat_Q$}, processing its VCSEL-wavelength-category-specific sample point set VCSEL_wavelength_specific_sample_points(Cat(j)) to compute therefrom a VCSEL-wavelength-category-specific particle-motion-descriptive signal $Cat_j$ (particle-motion) describing relative motion of the particles of the occluded blood from which the light of the VCSEL is scattered;

i. averaging the particle-motion-descriptive signals {$Cat_1$ (particle-motion) $\ldots Cat_Q$ (particle-motion)} to compute a multi-category-averaged particle-motion-descriptive signal; and j. computing the parameter from the multi-category-averaged particle-motion-descriptive signal.

A method for measuring at least one parameter that is (i) descriptive of stochastic motion of suspended particles within a fluid; and/or (ii) is a rheological property of the fluid or of the suspension; (iii) describes a concentration of suspended particles within the fluid; and/or (iv) is a diffusion coefficient of the suspended particles and/or (iv) is a viscosity of the fluid or of the suspension; and/or (v) is a food aging or spoilage parameter and/or (vii) is an in-vivo or in-vitro blood coagulation parameter, the method comprising:

a. supplying a time-fluctuating input current to a VCSEL to modulate a VCSEL output-wavelength according to VSCEL output-wavelength temporal-modulation-pattern;

b. illuminating the moving particles within the fluid by the VCSEL to generate an optical response of light scattered by the suspended and moving particles within the fluid;

c. receiving at least some of the moving-particles-scattered light into photodetector(s); and d. analyzing, in accordance with the VSCEL output-wavelength temporal-modulation-pattern, an electrical representation of the optical signal as derived from output of the photodetector(s) so as to compute the parameter.

In some embodiments, the VCSEL is operated in n Hz/m nm wavelength-fluctuation mode (n≥2) by varying an amount of electrical current delivered to the VCSEL to cause at least n distinct m nm wavelength-increase-decrease events per second where for each wavelength-increase-decrease event, an increase in an effective wavelength of the VCSEL of at least m nm is followed by a decrease of the effective wavelength of the VCSEL of at least m nm, a value of n being at least 2 (e.g. at least 3 or at least 5 or at least 10 or at least 20 or at least 50) and a value of m being at least 0.25 or at least 0.5 or at least 0.75 or at least 1, the time-dependence of an instantaneous amount of current defining a function I(t), the time-dependence of an instantaneous effective wavelength of the VCSEL being $\lambda_{EFFECTIVE}(t)$.

In some embodiments, the parameter is a blood parameter is selected from the group consisting of a blood plasma viscosity, a particle diffusion coefficient, and a coagulation parameter. In some embodiments, the parameter describes Brownian motion of the particles within the fluid. In some embodiments, the analysis of the electrical representation of the optical signal as derived from output of the photodetector(s) and/or the computing of the particle-motion-descriptive signals comprises computing at least the following functions of the sample-set-specific optical-response-descriptive electrical signals: (i) an autocorrelation function (ACF), (ii) a Hurst function; (iii) a fractal dimension; and (iv) an entropy.

Second Additional Discussion

Although teachings have been described mostly for in-vivo embodiments, this is not a limitation—the teachings, for example, may be applied in the context of Thromboelastography (TEG) is a method of testing the efficiency of blood coagulation. The teachings may be applied to particles other than RBCs and/or particles suspended in liquids other than blood plasma.

In another application, it is possible to measure an indication of food freshness—e.g. by measuring viscosity.

What is claimed is:

1. An in-vivo method for measuring at least one blood parameter, the method comprising:

a. operating a VCSEL in n Hz/m nm wavelength-fluctuation mode (n≥2) by varying an amount of electrical current delivered to the VCSEL to cause at least n distinct m nm wavelength-increase-decrease events per second where for each wavelength-increase-decrease event, an increase in an effective wavelength of the VCSEL of at least m nm is followed by a decrease of the effective wavelength of the VCSEL of at least m nm, a value of n being at least 2 and a value of m being at least 0.5, the time-dependence of an instantaneous amount of current defining a function I(t), the time-dependence of an instantaneous effective wavelength of the VCSEL being $\lambda_{EFFECTIVE}(t)$;

b. illuminating skin containing occluded blood by the VCSEL that is operating in n Hz/m nm wavelength-fluctuation mode to generate an optical response of light scattered by red blood cells (RBCs) within the occluded blood;

c. receiving at least some of the RBC-scattered light into photodetector(s) to generate an electrical representation of the optical signal; and d. sampling the electrical representation of the optical signal to obtain a sample point set Sample_Point_Set={$(st_1, MV(st_1)), (st_2, MV(st_2)),) \ldots (st_P, MV(st_P)),$} of sample points, each sample point $(st_i, MV(st_i))$ being an ordered pair where measurement value $MV(st_i)$ describes the optical signal at a different respective sampling-time $st_i$;

e. classifying each sample point $(st_i, MV(st_i))$ of the sample point set Sample_Point_Set, according to an instantaneous effective-wavelength $\lambda_{EFFECTIVE}(st_i)$ of the VCSEL at its sampling time $st_i$, into a VCSEL-wavelength category Cat(j) selected from a plurality of VCSEL-wavelength categories {$Cat_1 \ldots Cat_Q$};

f. for each given VCSEL-wavelength category $Cat_j$ of the plurality of VCSEL-wavelength categories {$Cat_1 \ldots Cat_Q$} forming, from the sample points classified into the given VCSEL-wavelength category Cat(j), a respective VCSEL-wavelength-category-specific sample point set VCSEL_wavelength_specific_sample_points(Cat(j)) of sample points {$(st_{1\_CAT(j)}, MV(st_{1\_CAT(j)}),(st_{2\_CAT(j)}), MV(St_{2\_CAT(j)}), \ldots$} g. for each given VCSEL-wavelength category $Cat_j$ of the plurality of VCSEL-wavelength categories {$Cat_1 \ldots Cat_Q$}, processing its VCSEL-wavelength-category-specific sample point set VCSEL_wavelength_specific_sample_points(Cat(j)) to compute therefrom a VCSEL-wavelength-category-specific RBC-motion-descriptive signal $Cat_j$(RBC-motion) describing relative motion of the RBCs of the occluded blood from which the light of the VCSEL is scattered;

i. averaging the RBC-motion-descriptive signals { $Cat_1$ (RBC-motion) $\ldots Cat_Q$ (RBC-motion)} to compute a multi-category-averaged RBC-motion-descriptive signal; and j. computing the blood parameter from the multi-category-averaged RBC-motion-descriptive signal.

2. The method of claim 1 wherein the blood parameter is selected from the group consisting of a blood plasma viscosity, an RBC diffusion coefficient, and a coagulation parameter.

3. The method of claim 1 wherein the parameter describes Brownian motion of a subject's red-blood cells within the subject's blood vessels.

4. The method of claim 1 wherein the skin is illuminated at a blood-flow restriction-location and the skin is illuminated downstream of the blood-flow restriction-location.

5. The method of claim 1 wherein the analysis of the electrical representation of the optical signal as derived from output of the photodetector(s) and/or the computing of the RBC-motion-descriptive signals comprises computing at least the following functions of the sample-set-specific optical-response-descriptive electrical signals: (i) an autocorrelation function (ACF), (ii) a Hurst function; (iii) a fractal dimension; and (iv) an entropy.

* * * * *